US006204282B1

(12) United States Patent
Neustadt et al.

(10) Patent No.: US 6,204,282 B1
(45) Date of Patent: Mar. 20, 2001

(54) BENZIMIDAZOLE COMPOUNDS THAT ARE VITRONECTIN RECEPTOR ANTAGONISTS

(75) Inventors: Bernard R. Neustadt, West Orange; Elizabeth M. Smith, Verona, both of NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/450,235

(22) Filed: Nov. 29, 1999

Related U.S. Application Data
(60) Provisional application No. 60/110,302, filed on Nov. 30, 1998.

(51) Int. Cl.$^7$ .................. A61K 31/4184; C07D 235/14; C07D 235/16
(52) U.S. Cl. ............... 514/394; 514/234.5; 544/139; 548/305.1; 548/309.7
(58) Field of Search .............. 548/309.7, 305.1; 544/139; 514/234.5, 394

(56) References Cited

U.S. PATENT DOCUMENTS

| | | | |
|---|---|---|---|
| 4,594,425 | * | 6/1986 | Musser et al. ............ 548/161 |
| 5,741,796 | * | 4/1998 | Hartman et al. ........... 514/435 |

FOREIGN PATENT DOCUMENTS

| | | | |
|---|---|---|---|
| 0 381 033 | 8/1990 | (EP) | ............ C07C/311/19 |
| 0 478 328 | 4/1992 | (EP) | ............ C07C/271/22 |
| 0 528 586 | 2/1993 | (EP) | ............ A61K/31/325 |
| 0 528 587 | 2/1993 | (EP) | ............ A61K/31/19 |
| 0 529 858 | 3/1993 | (EP) | ............ C07D/241/08 |
| 0 540 334 | 5/1993 | (EP) | ............ C07D/209/46 |
| 0 542 363 | 5/1993 | (EP) | ............ C07D/211/26 |
| 0 635 492 | 1/1995 | (EP) | ............ C07D/217/24 |
| WO 93/00095 | 1/1993 | (WO) | ............ A61K/31/55 |
| WO 93/08174 | 4/1993 | (WO) | ............ C07D/243/14 |
| WO 95/04057 | 2/1995 | (WO) | ............ C07D/487/04 |
| WO 95/32710 | 12/1995 | (WO) | ............ A61K/31/18 |
| WO 96/00730 | 1/1996 | (WO) | ............ C07D/519/00 |

OTHER PUBLICATIONS

Ross et al., "Interactions Between the Bone Matrix Proteins Osteopontin and Bone Sialoprotein and the Osteoclast Integrin Alpha v Beta 3 Potentiate Bone Resorption", *Journal of Biological Chemistry*, vol. 268, pp. 9901–9901 (1993).
D.R. Phillips et al., "The Platelet Membrane Glycoprotein IIb–IIIb Complex," *Blood*, vol. 71, No. 4, pp. 831–843 (1988).
M. Sato et al., "Echistatin is a Potent Inhibitor of Bone Resorption in Culture," *The Journal of Cell Biology*, vol. III, pp. 1713–1723 (1990).
M.A. Horton et al., "Arg–Gly–Asp (RGD) Peptides and the Anti–Vitronectin Receptor Antibody 23C6 Inhibit Dentine Resorption and Cell Spreading by Osteoclasts," *Experimental Cell Research*, vol. 195, pp. 368–375 (1991).

D.R. Bertolini et al., "Inhibition of Bone Resorption by Synthetic RGD Containing Peptides," *Journal of Bone and Mineral Research*, vol. 6, Suppl. 1 (1991).

(List continued on next page.)

*Primary Examiner*—Laura L. Stockton
(74) *Attorney, Agent, or Firm*—William Lee; Arthur Mann

(57) ABSTRACT

The present invention provides compounds having the formula

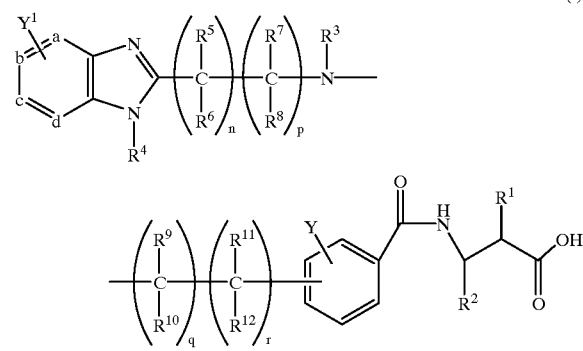

wherein n, p, q and r are each independently selected from 0 or 1;

a, b, c, and d each independently represents a carbon or nitrogen atom, with the proviso that no more than two of a, b, c, and d are nitrogen atoms;

Y and $Y^1$ each independently represents 1–4 optional substituents selected from alkyl, alkoxy, halo, —$CF_3$, and —C(O)OH;

$R^1$, $R^2$, $R^3$ and $R^4$ are as defined herein;

$R^5$, $R^6$, $R^7$, $R^8$, $R^9$, $R^{10}$, $R^{11}$ and $R^{12}$ are independently selected from H or $C_1$–$C_3$ alkyl;

and wherein

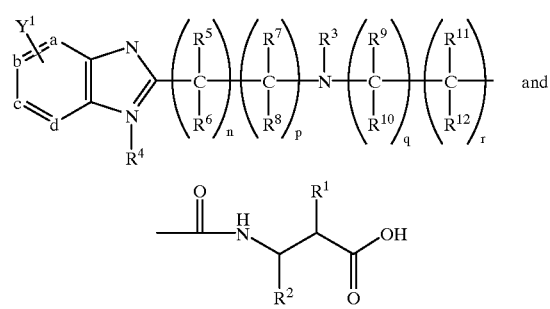

are positioned meta or para relative to each other;

or a biolabile ester thereof, or a pharmaceutically acceptable salt thereof. Also provided are methods of using these compounds for treating vitronectin-mediated disorders, e.g., cancer, retinopathy, atherosclerosis, vascular restenosis, and osteoporosis.

22 Claims, No Drawings

OTHER PUBLICATIONS

J.E. Fisher et al., "Inhibiton of Osteoclastic Bone Resorption in Vivo by Schistatin, an 'Arginyl–Glycyl–Aspartyl' (RGD-)–Containing Protein," *Endocrinology*, vol. 132, No. 3, pp. 1411–1413 (1993).

S.L. Brown et al., "Stimulation of Migration of Human aortic Smooth Muscle Cells by Vitronectin: Implications for Atherosclerosis," *Cardiovascular Research*, vol. 28, pp. 1815–1820 (1994).

P.C. Brooks et al., "Intefrin $\alpha_v\beta_3$ Antagonists Promote Tumor Regression by Inducing Apoptosis of Angiogenic Blood Vessels," *Cell*, vol. 79, pp. 1157–1164 (1994).

K.C. Nicolaou et al., "Design, Synthesis and Biological Evaluation of Nonpeptide Integrin Antagonists," *Bioorganic & Medicinal Chemistry*, vol. 6, pp. 1185–1208 (1998).

* cited by examiner

BENZIMIDAZOLE COMPOUNDS THAT ARE VITRONECTIN RECEPTOR ANTAGONISTS

This application claims the benefit of U.S. Provisional Application No. 60/110,302, filed Nov. 30, 1998.

FIELD OF THE INVENTION

This invention relates to compounds which are vitronectin receptor antagonists and are useful for the treatment of cancer, retinopathy, cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpIIb/IIIa, also known as the "fibrinogen receptor," and $\alpha_v\beta_3$, also known as the "vitronectin receptor." The fibrinogen receptor gpIIb/IIIa is expressed on the platelet surface, and it mediates platelet aggregation and the formation of a hemostatic clot at the site of a bleeding wound. Philips, et al., *Blood.*, 1988, 71, 83 1. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the bone resorption process and contributes to the development of osteoporosis. Ross, et al., *J. Biol, Chem.*, 1987, 262, 7703. The $\alpha_v\beta_3$ receptor expressed on human aortic smooth muscle cells stimulates their migration into neointima, which leads to the formation of atherosclerosis and restenosis after angioplasty. Brown et al., *Cardiovascular Res.*, 1994, 28, 1815. Additionally, a recent study has shown that a $\alpha_v\beta_3$ antagonist is able to promote tumor regression by inducing apoptosis of angiogenic blood vessels. Brooks, et al., *Cell,* 1994, 79, 1157. Thus, agents that would block the vitronectin receptor would be useful in treating diseases mediated by this receptor, such as osteoporosis, atherosclerosis, restenosis and cancer.

The vitronectin receptor is known to bind to bone matrix proteins, such as osteopontin, bone sialoprotein and thrombospondin, which contain the tri-peptide Arg—Gly—Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J Cell Biol.* 1990, 111, 1713 disclose that echistatin, a snake venom peptide which contains the RGD sequence, is a potent inhibitor of bone resorption in tissue culture, and inhibits attachment of osteoclasts to bone. Fisher, et al., *Endocrinology* 1993, 132, 1411, has further shown that echistatin inhibits bone resorption in vivo in the rat. Bertolini et al., *J Bone Min. Res.*, 6, Sup. 1, S146, 252 have shown that cyclo-S,S—N$^\alpha$- acetyl-cysteinyl-N$^\alpha$-methyl-argininyl-glycyl-aspartyl-penicillamine inhibits osteoclast attachment to bone. EP 0 528 587 and EP 0 528 586 report substituted phenyl derivatives which inhibit osteoclast mediated bone resorption.

Alig et al., EP 0 381 033, Hartman, et al., EP 0 540 334, Blackburn, et al., WO 93/08174, Bondinell, et al., WO 93/00095, Blackburn, et al., WO 95/04057, Egbertson, et al., EP 0 478 328, Sugihara, et al., EP 0 529 858, Porter, et al., EP 0 542 363, and Fisher, et al., EP 0 635 492 disclose certain compounds that are useful for inhibiting the fibrinogen receptor. WO 96/00730 discloses certain compounds that are vitronectin receptor antagonists.

SUMMARY OF THE INVENTION

We have invented novel compounds that are antagonists at the vitronectin receptor, i.e., they have a high affinity for the vitronectin receptor, thereby making them useful for treating disorders or diseases mediated by the vitronectin receptor, e.g., cancer, retinopathy, artherosclerosis, vascular restenosis and osteoporosis. The compounds of our invention have the formula:

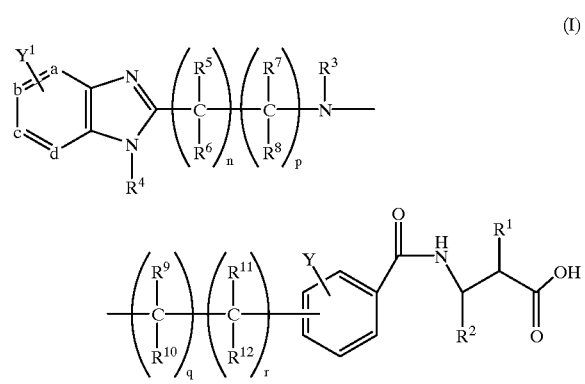

wherein n, p, q and r are each independently selected from 0 or 1;

a, b, c, and d each independently represents a carbon or nitrogen atom, with the proviso that no more than two of a, b, c, and d are nitrogen atoms;

Y and $Y^1$ each independently represents 1–4 optional substituents selected from alkyl, alkoxy, halo, —$CF_3$, and —C(O)OH;

$R^1$ is H, alkyl, aryl, aralkyl, arylcycloalkyl, heteroaryl, cycloalkyl, heterocycloalkyl, heteroaralkyl, cycloalkylalkyl, heterocycloalkylalkyl, —NHR$^A$, —NHC(O)R$^A$, —NHSO$_2$R$^A$, NHC(O)NHR$^A$ or —NHC(O)OR$^A$, $R^1$ being optionally substituted by 1–3 groups selected from halo, alkyl, —CF$_3$, —CN, —OR$^B$, —SR$^B$, —CO$_2$R$^B$, —C(O)R$^B$, —OC(O)R$^B$, —OC(O)OR$^B$ and —SO$_2$R$^B$, and R$^A$ and R$^B$ are independently selected from H, alkyl, aryl, aralkyl, arylcycloalkyl, heteroaryl, cycloalkyl, heterocycloalkyl, heteroaralkyl, cycloalkylalkyl or heterocycloalkylalkyl, with the proviso that when $R^1$ is alkyl, $R^1$ is not substituted with halo, the proviso that when $R^1$ is —NHSO$_2$R$^A$ or —NHC(O)OR$^A$, R$^A$ is not H, and the proviso that for —SO$_2$R$^B$ or —OC(O)OR$^B$, R$^B$ is not H;

$R^2$ is H, alkyl, aryl, aralkyl, arylcycloalkyl, heteroaryl, cycloalkyl, heterocycloalkyl, heteroaralkyl, cycloalkylalkyl, or heterocycloalkylalkyl, $R^2$ being optionally substituted by 1–3 groups selected from halo, alkyl, —CF$_3$, —CN, —OR$^C$, —SR$^C$, —CO$_2$R$^C$, —C(O)R$^C$, —OC(O)R$^C$, —OC(O)OR$^C$ and —SO$_2$R$^C$, wherein R$^C$ is selected from H, alkyl, aryl, aralkyl, arylcycloalkyl, heteroaryl, cycloalkyl, heterocycloalkyl, heteroaralkyl, cycloalkylalkyl or heterocycloalkylalkyl, with the proviso that when $R^2$ is alkyl, $R^2$ is not substituted with halo, and the proviso that for —SO$_2$R$^C$ or —OC(O)OR$^C$, R$^C$ is not H;

$R^3$ is H, alkyl, aralkyl, arylcycloalkyl, cycloalkylalkyl, heterocycloalkylalkyl, heteroaralkyl, aryl, heteroaryl, cycloalkyl, heterocycloalkyl, —C(O)R$^D$, —C(O)OR$^D$, —SO$_2$R$^E$, —C(O)NR$^F$ R$^G$, —C(O)NR$^F$SO$_2$R$^E$, or —C(=S)NR$^F$R$^G$, wherein R$^D$, R$^E$, R$^F$ and R$^G$ are independently selected from H, alkyl, aryl, aralkyl, arylcycloalkyl, heteroaryl, cycloalkyl, heterocycloalkyl, cycloalkylalkyl or heterocycloalkylalkyl, or R$^F$ and R$^G$ taken together complete a 5–7 member ring containing 0 to 1 oxygen or sulfur atoms, and 1 to 2 nitrogen atoms, $R^3$ being optionally substituted by 1–3 groups selected from halo, alkyl, aryl, —$CF_3$, —CN, —$OR^H$, —$SR^H$, —$CO_2R^H$, —$C(O)R^H$, —$OC(O)R^H$, —$OC(O)OR^H$, —$SO_2R^H$ and —$NR^HR^H$, wherein $R^H$ is selected from H, alkyl, aryl, aralkyl, arylcycloalkyl, heteroaryl, cycloalkyl, heterocycloalkyl, heteroaralkyl, cycloalkylalkyl or heterocycloalkylalkyl, with the proviso that when $R^3$ is alkyl, $R^3$ is not substituted with halo, the proviso that when $R^3$ is —$SO_2R^E$, —$C(O)NR^FSO_2R^E$, or —$CO(O)R^D$, $R^D$ and $R^E$ are not H, and the proviso that for —$SO_2R^H$ or —$OC(O)OR^H$, $R^H$ is not H;

$R^4$ is H, alkyl, aralkyl, arylcycloalkyl, cycloalkylalkyl, heterocycloalkylalkyl, heteroaralkyl, aryl, heteroaryl, cycloalkyl, or heterocycloalkyl, $R^4$ being optionally substituted by 1–3 groups selected from halo, alkyl, —$CF_3$, —CN, —$OR^J$, —$SR^J$, —$CO_2R^J$, —$C(O)R^J$, —$OC(O)R^J$, —$OC(O)OR^J$ and —$SO_2R^J$, wherein $R^J$ is selected from H, alkyl, aryl, aralkyl, arylcycloalkyl, heteroaryl, cycloalkyl, heterocycloalkyl, heteroaralkyl, cycloalkylalkyl or heterocycloalkylalkyl, with the proviso that when $R^4$ is alkyl, $R^4$ is not substituted with halo, and the proviso that for —$SO_2R^J$ or —$OC(O)OR^J$, $R^J$ is not H;

$R^5$, $R^6$, $R^7$, $R^8$, $R^9$, $R^{10}$, $R^{11}$ and $R^{12}$ are independently selected from H or $C_1$–$C_3$ alkyl;

and wherein

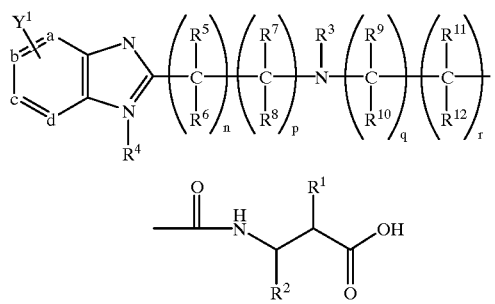

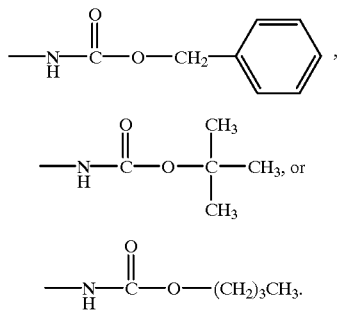

are positioned meta or para relative to each other; or a biolabile ester thereof, or a pharmaceutically acceptable salt thereof.

DETAILED DESCRIPTION OF THE INVENTION $R^1$ is preferably H, —$NHR^A$, —$NHC(O)R^A$, —$NHC(O)OR^A$, —$NHC(O)NHR^A$, or —$NHSO_2R^A$. $R^1$ is more preferably —$NHC(O)OR^A$. $R^1$ is most preferably,

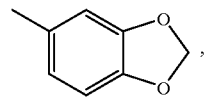

$R^2$ is preferably H.

$R^3$ is preferably selected from H, alkyl, —$C(O)R^D$, —$C(O)OR^D$, —$C(O)NR^FR^G$, and —$C(=S)NR^FR^G$. $R^D$ is preferably selected from phenyl, alkyl, aralkyl, arylcycloalkyl, cycloalkyl, and

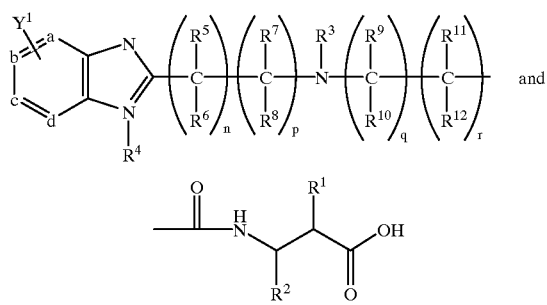

wherein $R^D$ is optionally substituted by 1–3 substituents selected from alkoxy, halo, cycoalkyl, —S—$CH_3$, phenyloxy, —$OC(O)CH_3$, —$C(O)OC_2H_5$ and —$N(CH_3)_2$. $R^F$ and $R^G$ are preferably selected from H, alkyl, phenyl, cycloalkyl, and aralkyl, wherein $R^F$ and $R^G$ are optionally substituted by alkoxy, halo or —$CO_2R^H$.

$R^4$ is preferably H or alkyl, most preferably H.

$R^5$, $R^6$, $R^7$, $R^8$, $R^9$, $R^{10}$, $R^{11}$ and $R^{12}$ are each preferably H.

Preferably, the sum of n+p is 1.

Preferably, the sum of q+r is 1.

Preferably, a, b, c, and d are carbon atoms.

Preferably, are positioned para relative to each other.

The following compounds, including biolabile esters, or pharmaceutically acceptable salts thereof, are particularly preferred:

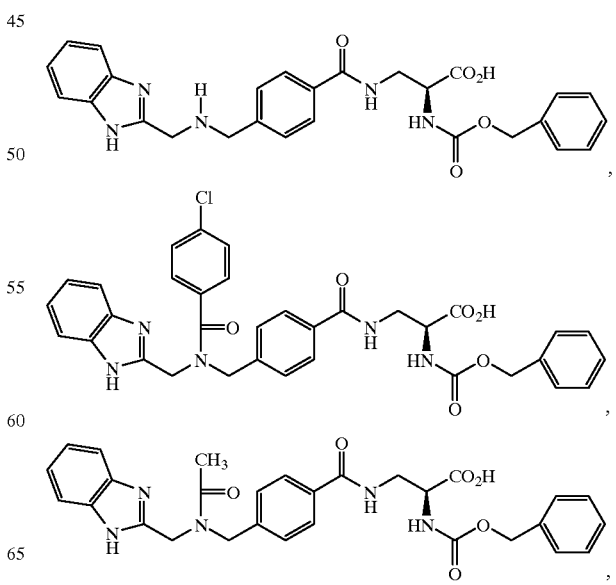

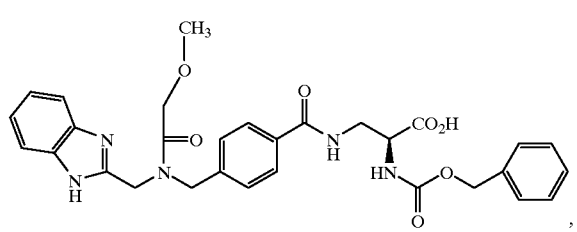
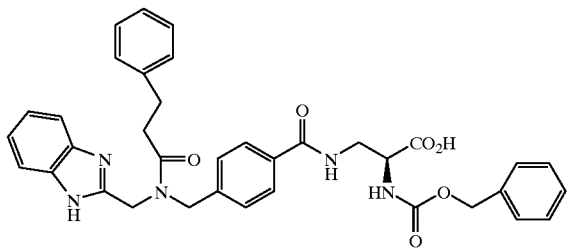
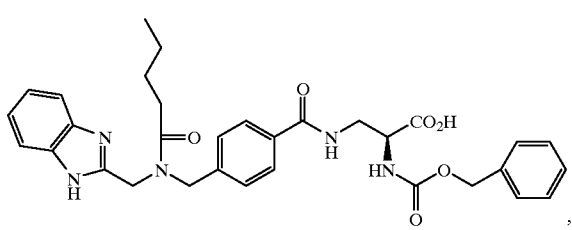
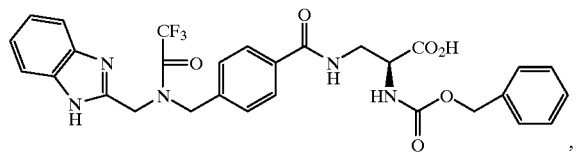
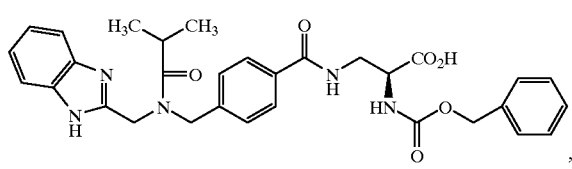
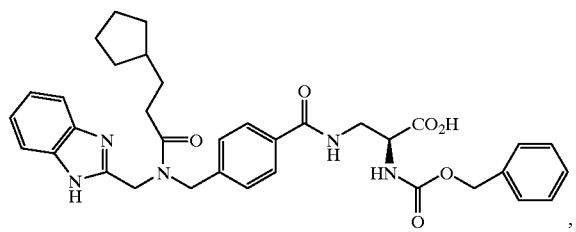
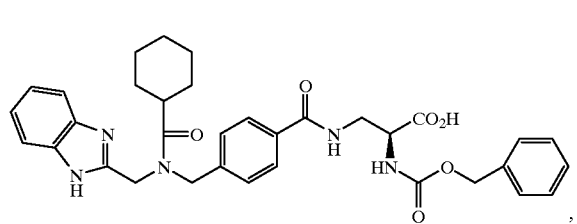

-continued

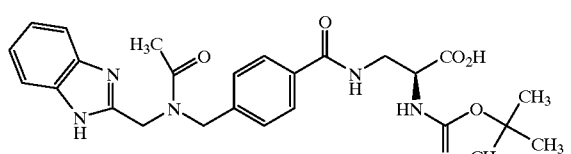
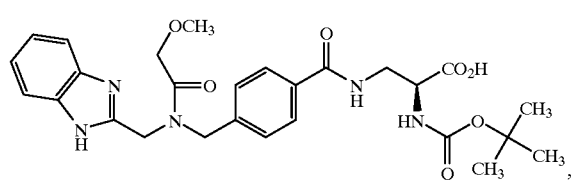
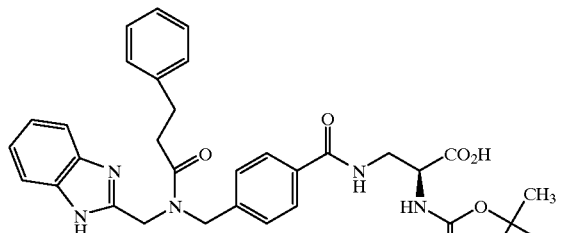
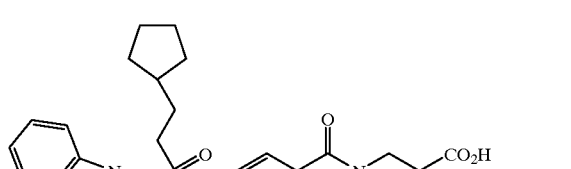
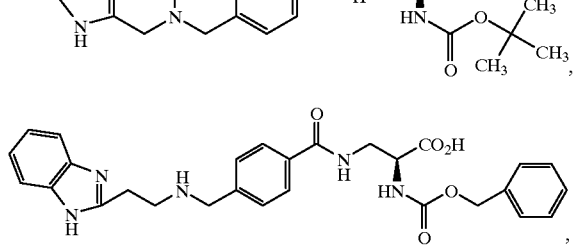
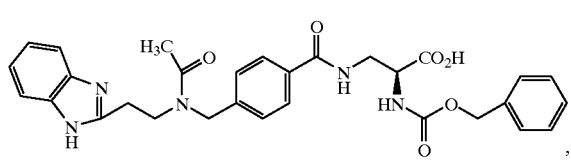
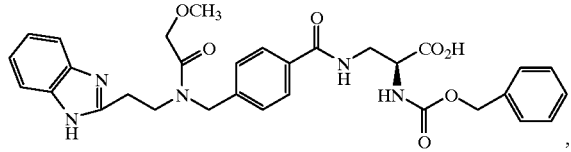
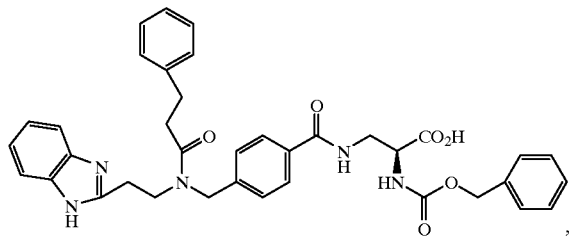
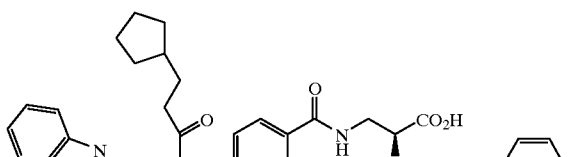
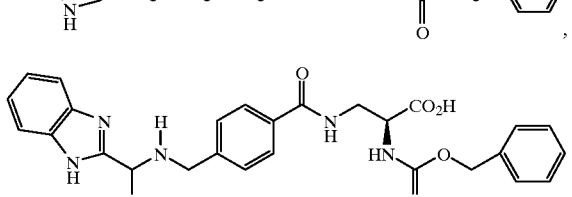
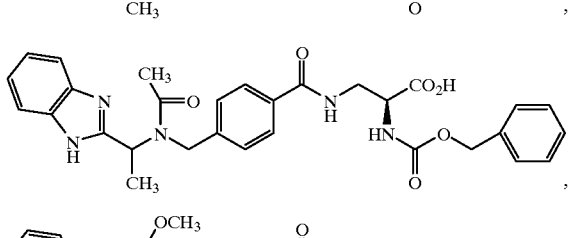
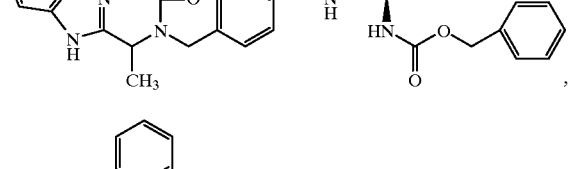
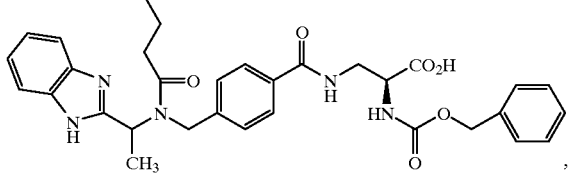
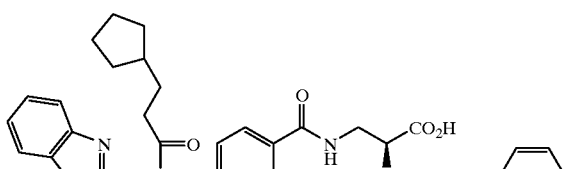
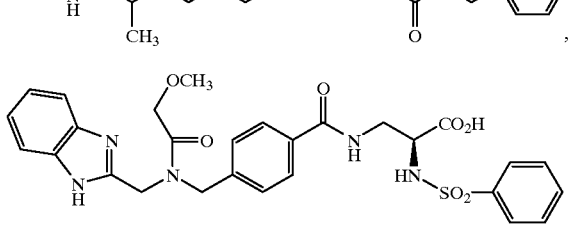
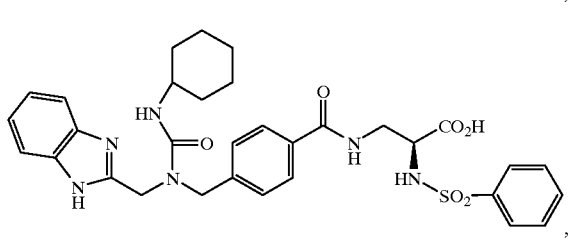

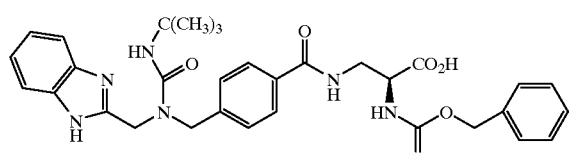,
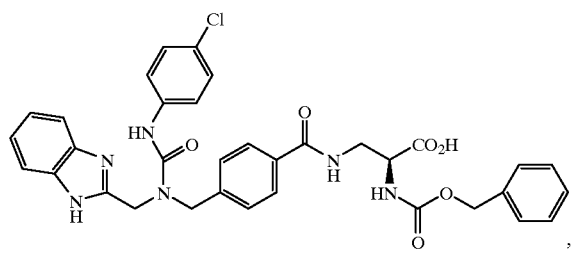,
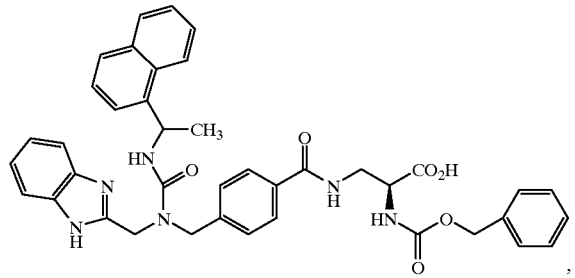,
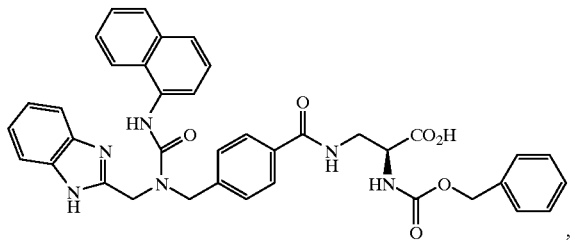,
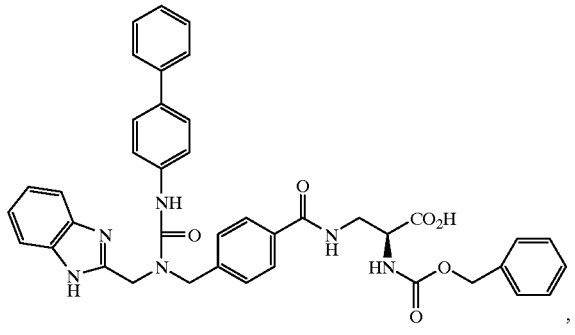,
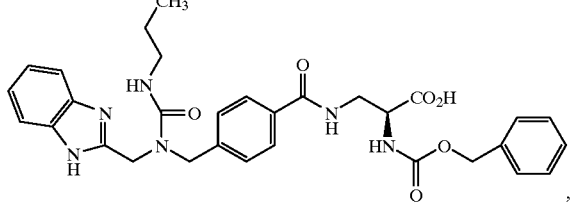,
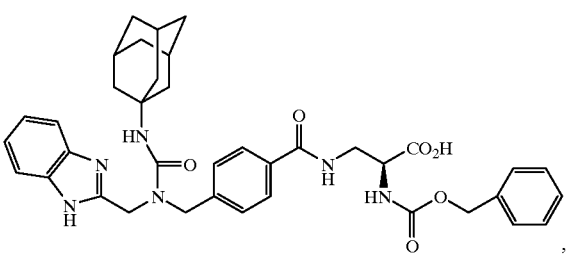,
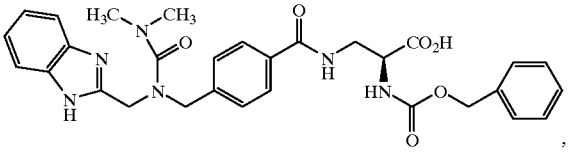,
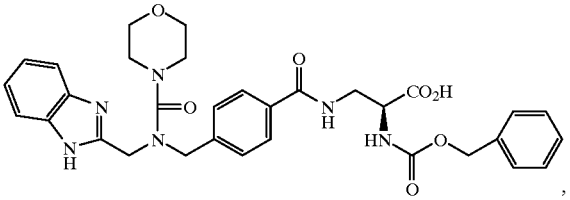,
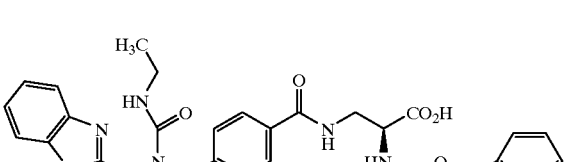,
,
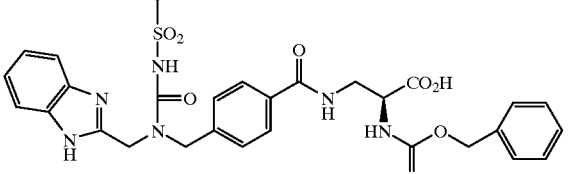,
,
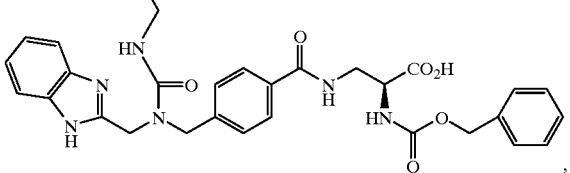,

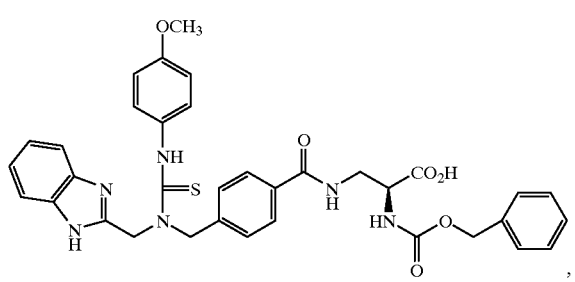
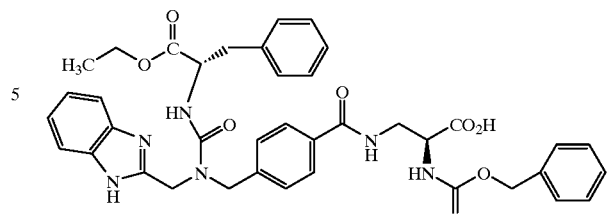
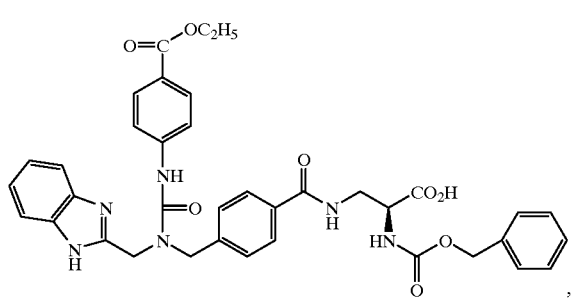
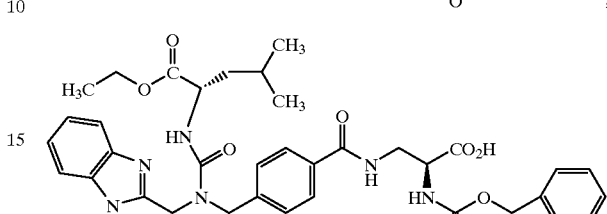
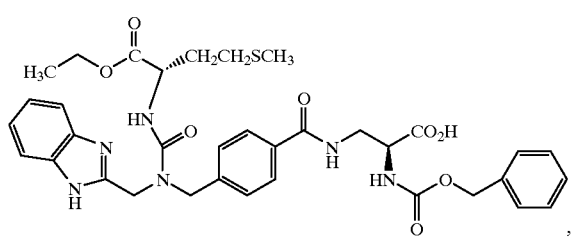
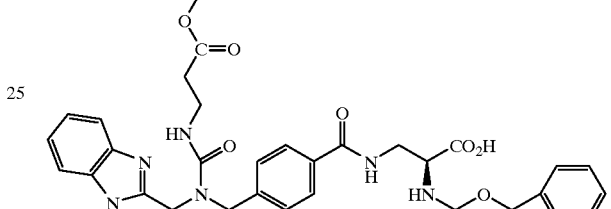
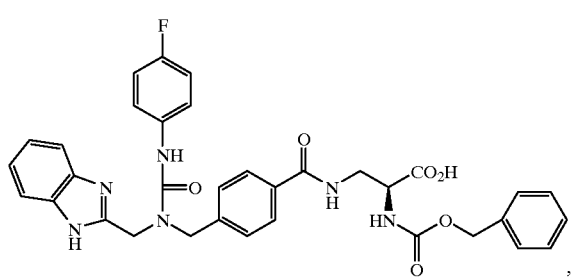
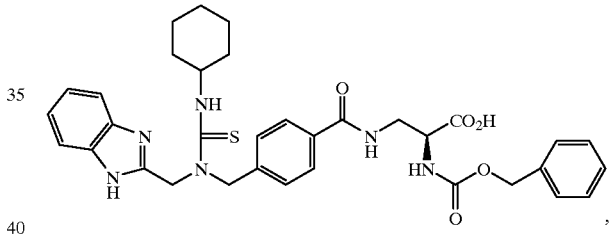
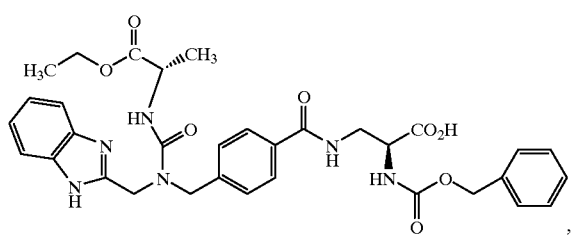
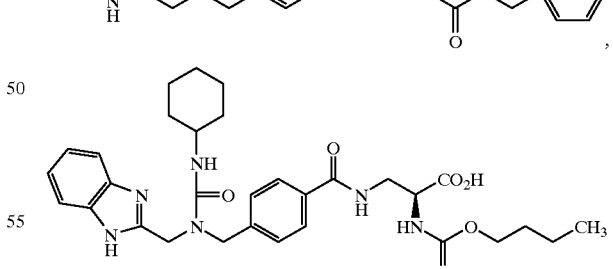
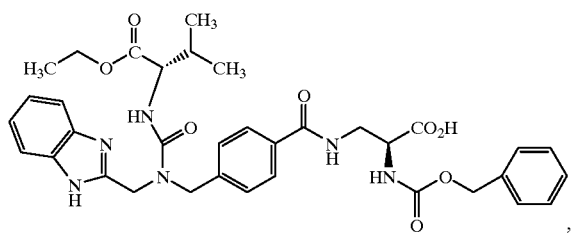
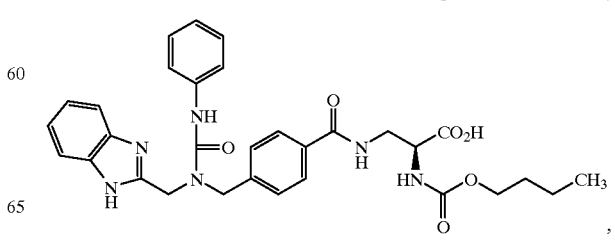

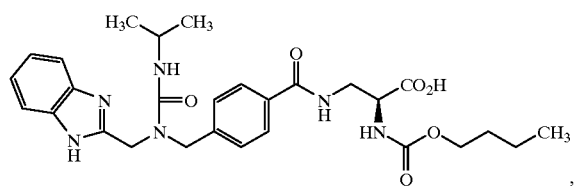,
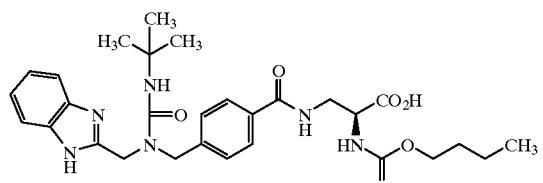,
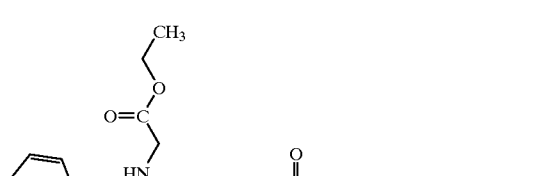,
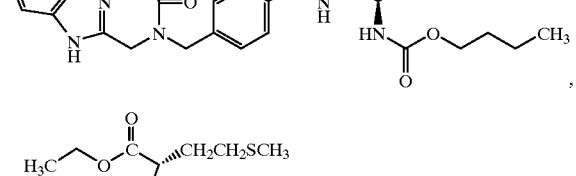,
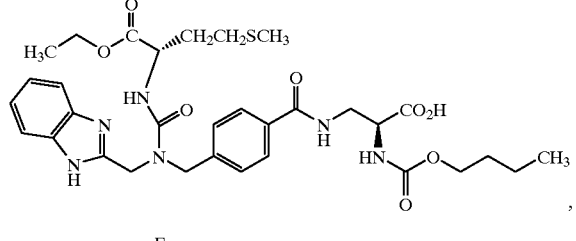,
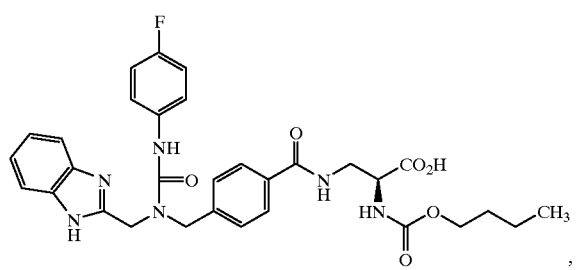,
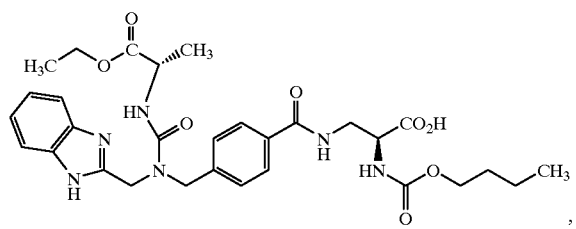,
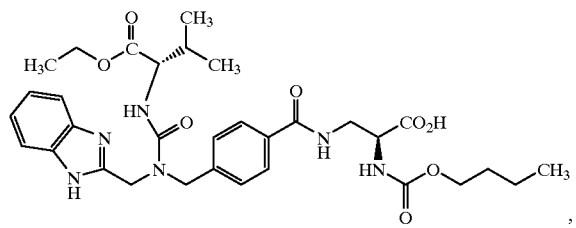,
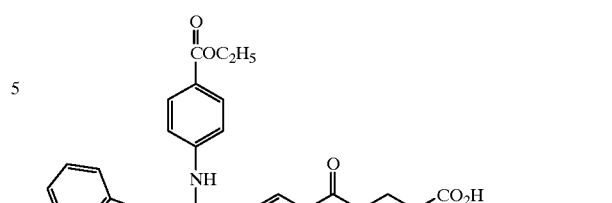,
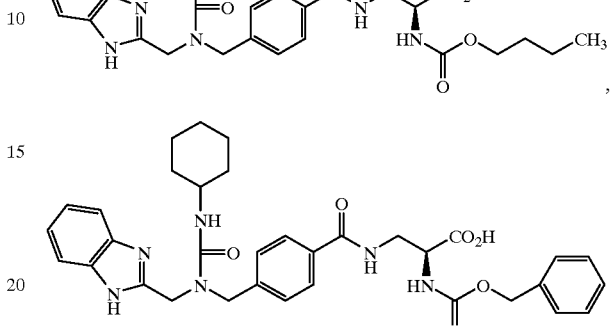,
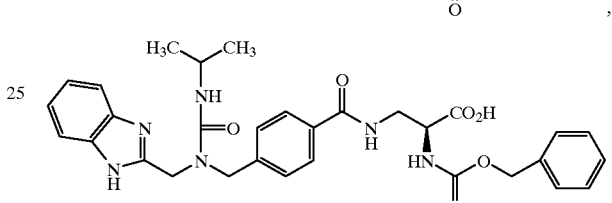,
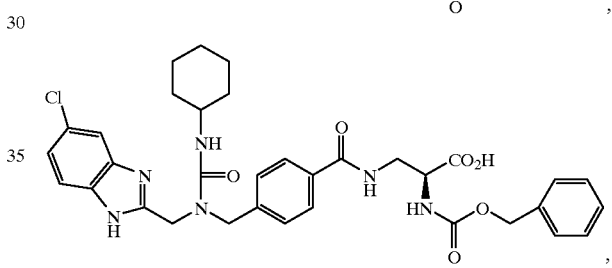,
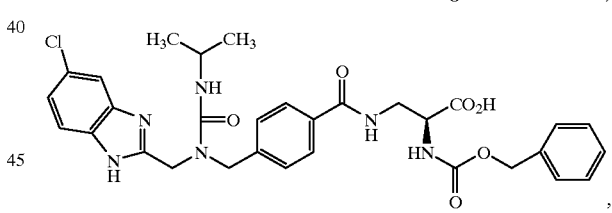,
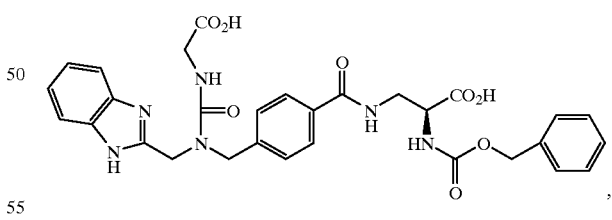,
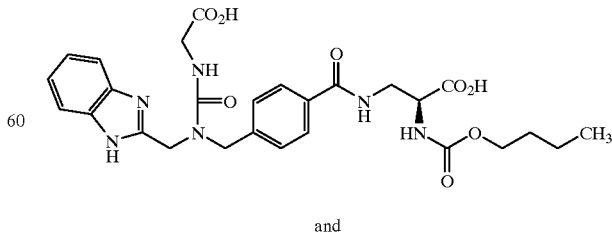
and

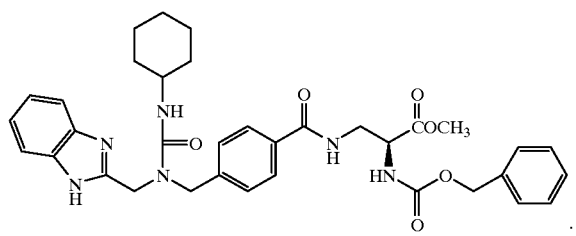

Of the foregoing,

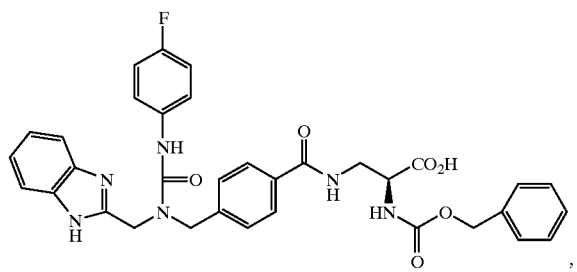

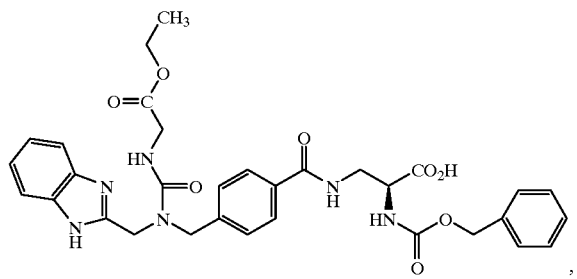

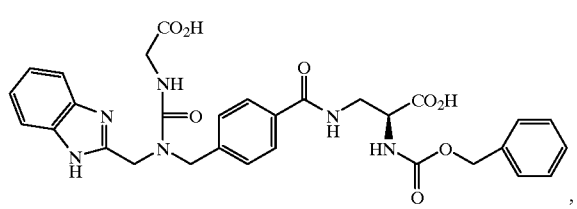

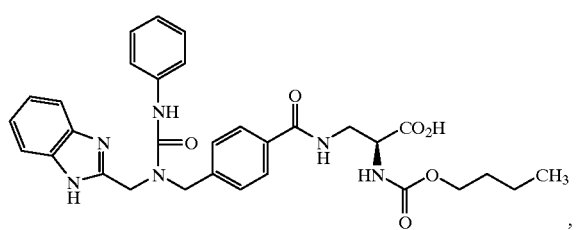

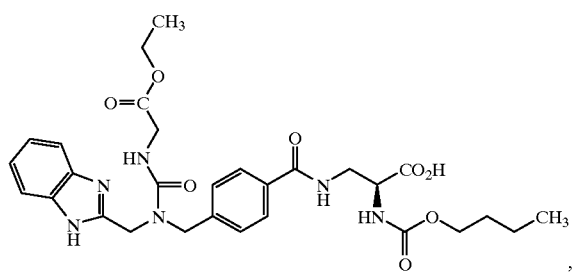

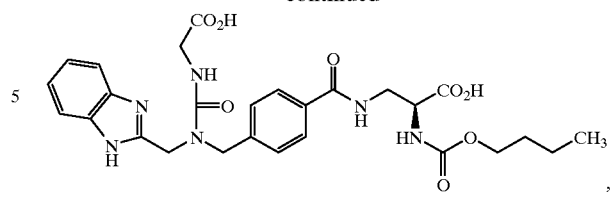

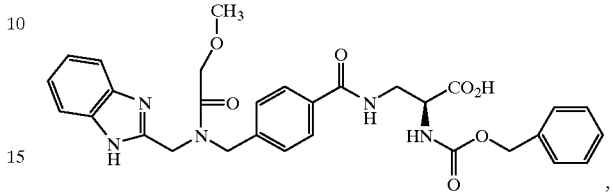

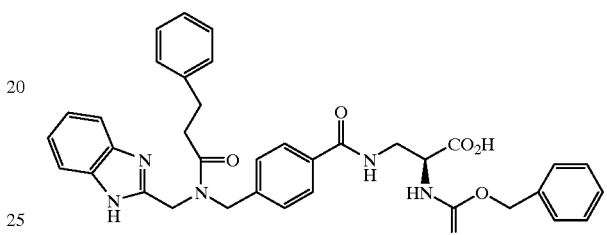

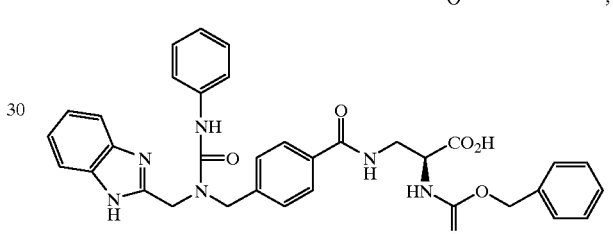

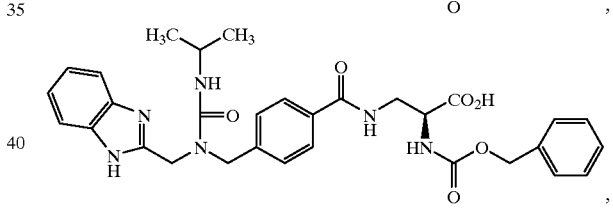

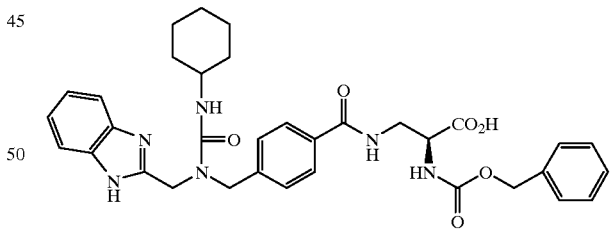

and

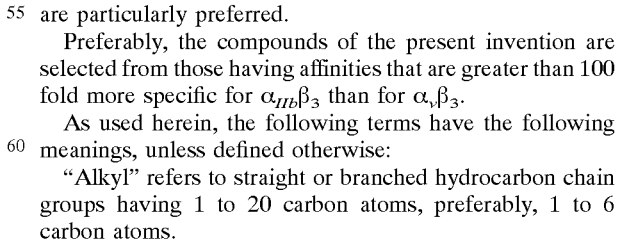

are particularly preferred.

Preferably, the compounds of the present invention are selected from those having affinities that are greater than 100 fold more specific for $\alpha_{IIb}\beta_3$ than for $\alpha_v\beta_3$.

As used herein, the following terms have the following meanings, unless defined otherwise:

"Alkyl" refers to straight or branched hydrocarbon chain groups having 1 to 20 carbon atoms, preferably, 1 to 6 carbon atoms.

"Alkoxy" refers to groups having the formula —OR, wherein R is alkyl.

"Aryl" refers to carbocyclic groups having at least one aromatic ring.

"Aralkyl" refers to groups having the formula aryl-R—, wherein R is alkyl.

"Arylcycloalkyl" refers to groups having the formula aryl-R—, wherein R is cycloalkyl.

"Arylalkoxy" refers to groups having the formula aryl-R—O—, wherein R is alkyl.

"Carboxy" refers to a group having the formula —C(O)OH.

"Carboxyalkyl" refers to groups having the formula, —R—C(O)OH, wherein R is alkyl.

"Carbamoyl" refers to a group having the formula —C(O)NH$_2$.

"Carbamoylalkyl" refers to groups having the formula —R—C(O)NH$_2$, wherein R is alkyl.

"Cbz" refers to benzyloxycarbonyl.

"Cycloalkyl" refers to a non-aromatic carbocyclic ring or multi-carbocyclic ring system of from 3 to 20 carbon atoms, preferably, 3 to 7 carbon atoms.

"Cycloalkylalkyl" refers to groups having the formula cycloalkyl-R—, wherein R is alkyl.

"Fmoc" refers to 9-fluorenylmethoxycarbonyl.

"Heteroaryl" refers to aromatic carbocyclic groups, wherein one or more of the carbon atoms of such groups are replaced with a heteroatom selected from O, S and N.

"Heteroaralkyl" refers to groups having the formula heteroaryl-R—, wherein R is alkyl.

"Heterocycloalkyl" refers to a cycloalkyl group, wherein one or more of the carbon atoms of such group is replaced with O, S, NH, or N-alkyl.

"Heterocycloalkylalkyl" refers to groups having the formula heterocycloalkyl-R—, wherein R is alkyl.

"Halo" refers to a halogen substituent.

The term "biolablile ester" means a pharmaceutically acceptable, biologically degradable ester derivative of a compound of formula (I), that is a prodrug which, upon administration to a animal or human being, is converted in the body to a compound of formula (I).

The term "vitronectin—mediated disorder" refers to a disease state or malady which is caused or exacerbated by a biological activity of vitronectin receptors. Disorders mediated by the vitronectin receptor include, without limitation, cancer, retinopathy, artherosclerosis, vascular restenosis, and osteoporosis.

The term "effective amount" refers to an amount of vitronectin receptor antagonist compound sufficient to exhibit a detectable therapeutic effect. The therapeutic effect may include, for example, without limitation, inhibiting the growth of undesired tissue or malignant cells, or increasing bone density. The precise effective amount for a subject will depend upon the subject's size and health, the nature and severity of the condition to be treated, and the like. The effective amount for a given situation can be determined by routine experimentation based on the information provided herein.

The following abbreviations are used for the solvents and reagents discussed herein: ethanol ("EtOH"); methanol ("MeOH"); acetic acid ("AcOH"); ethyl acetate ("EtOAc"); 2-(1H-benzotriazole-1-yl)-1,1,3,3-tetrarnethyluronium hexafluorophosphate ("HBTU"); 1-hydroxybenzotriazole ("HOBt"); bromo-tris-pyrrolidino-phosphonium hexafluorophosphate ("PyBroP"); N,N-dimethylformamide ("DMF"); trifluoroacetic acid ("TFA"); 1-(3-dimethylaminopropyl)-3-ethylcarbodiimide hydrochloride ("EDCI"); and diisopropylethylamine ("DIPEA"). In addition, "Ph" represents a phenyl group; "tBu" represents a —C(CH$_3$)$_3$ group; "OtBu" represents an —O—C(CH$_3$)$_3$ group, "n-Bu" or "Bu-n" represents an n-butyl group, "Et" represents an ethyl group, "Me" represents a methyl group, "Ac" represents an acetyl group, and "Boc" represents t-butoxycarbonyl.

The compounds of the invention have asymmetric carbon atoms, and therefore, all isomers, including enantiomers and diastereomers are within the scope of this invention. The invention includes d and l isomers in both pure form and in admixture, including racemic mixtures. Isomers can be prepared using conventional techniques, either by reacting chiral starting materials, or by separating isomers of compounds of formula (I).

Certain compounds of the present invention will be acidic in nature (e.g., those which have a carboxyl or phenolic hydroxyl group). These compounds form pharmaceutically acceptable salts with inorganic and organic bases. The salt may be prepared by treating a solution of the compound with the appropriate base. Non-limitative examples of such salts are sodium, potassium, calcium, aluminum, gold and silver salts, and salts formed with pharmaceutically acceptable amines such as ammonia, alkyl amines, hydroxyalkylamines, N-methylglucamine and the like.

Certain compounds of the invention will be basic in nature, and may form pharmaceutically acceptable salts with organic and inorganic acids. Non-limitative examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt.

It may be desirable when providing the compounds of the invention for ora administration to use the compounds of formula (I) in the form of a biolabile ester. The suitability of any particular ester—forming group can be assessed by conventional in vivo animal or in vitro enzyme hydrolysis studies. Thus, desirably, for optimum effect, the ester should only be hydrolysed after absorption is complete. Accordingly, the ester should be resistant to premature hydrolysis by digestive enzymes before absorption, but should be productively hydrolysed by, for example, gutwall, plasma or liver enzymes. In this way, the active acid is released into the bloodstream following oral absorption of the prodrug.

Suitable biolabile esters may include alkyl, alkanoyloxyalkyl, cycloalkanoyloxyalkyl, aroyloxyalkyl and alkoxycarbonyloxyalkyl esters, including cycloalkyl and aryl substituted derivatives thereof, aryl esters and cycloalkyl esters, wherein said alkyl, alkanoyl or alkoxy groups may contain from 1 to 8 carbon atoms and be branched-chain or straight—chain, said cycloalkyl groups may contain from 3–7 carbon atoms and said cycloalkanoyl groups from 4–8 carbon atoms wherein both are optionally benzo-fused, and said aryl and aroyl groups include substituted phenyl, naphthyl or indanyl ring systems. Preferably, the biolabile esters of the invention are C$_1$–C$_4$ alkyl esters. More preferably, they are methyl, ethyl and pivaloyloxymethyl esters.

Biolabile esters may be obtained from the acids of formula (I) by standard reactions well known to persons skilled in the art. For example, aryl and alkyl esters can be synthesized via activation of a carboxylic acid group of (I) in a variety of ways, such as by forming the acyl chloride, followed by reaction with the required phenol or alcohol.

Alternatively, alkyl esters are obtainable by alkylation of a suitable alkali, or alkaline earth, metal carboxylate salt of a compound of formula (I).

The compounds of the present invention may be prepared according to the following reaction scheme (Scheme I):

In Scheme 1, which depicts a solid phase preparation of compounds wherein at least one of q or r is 1, compound 2 is attached by conventional means to a polymeric resin 3 (e.g., a cross—linked polystyrene or a polyethylene glycol/polystyrene copolymer) through a cleavable acid labile

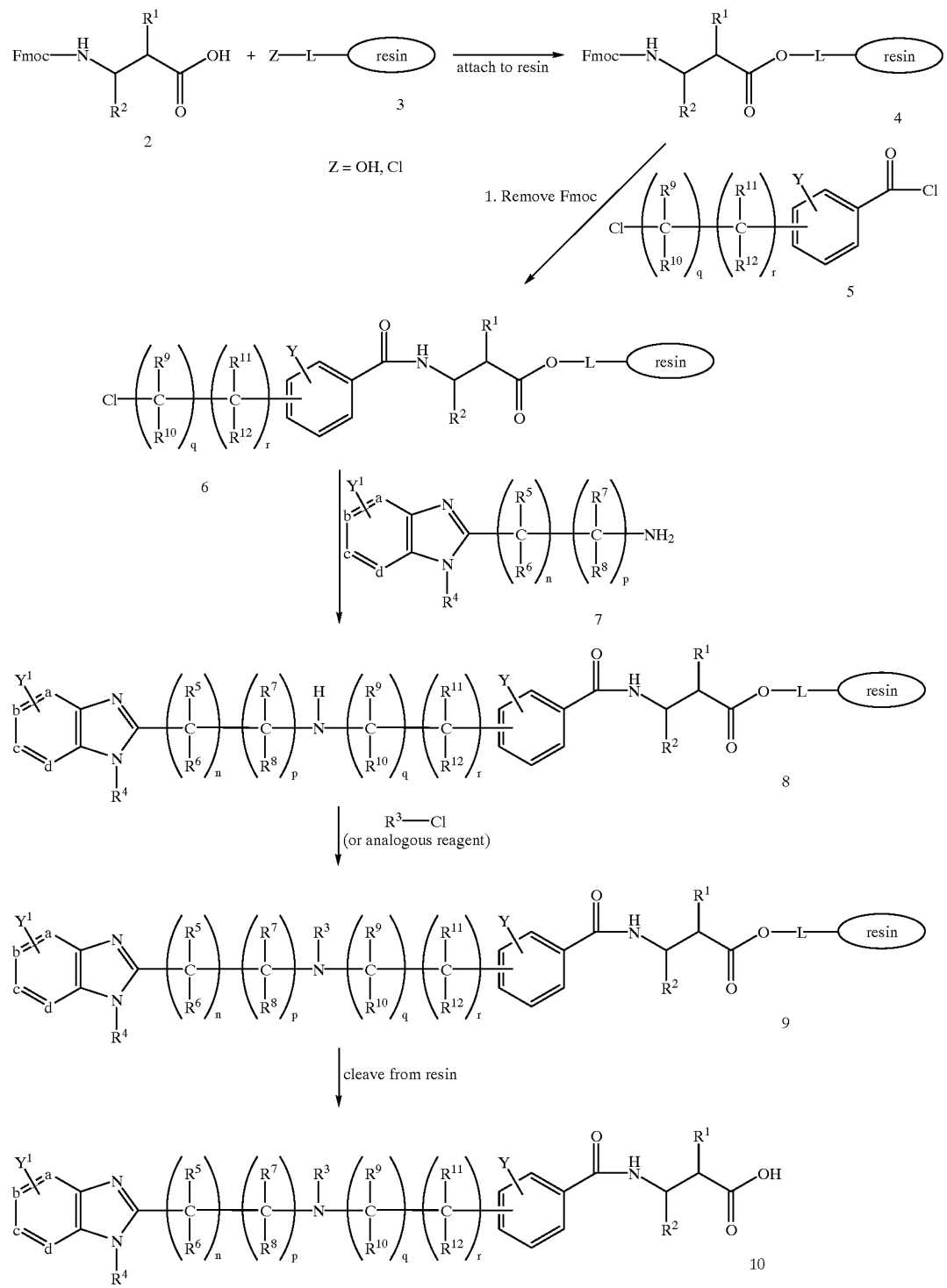

linker, L, having an —OH or —Cl group, e.g., Wang, Sasrin and chlorotrityl resin, to form resin compound 4. For example, the attachment to the resin may be carried out by reacting compound 2 with the resin 3 (Cl-form) in the presence of DIPEA in an organic solvent, e.g., DMF or methylene chloride. The Fmoc group of compound 4 is removed by conventional means, e.g., by treating with piperidine in DMF at 0° to 80° C., and acylated with benzoyl chloride 5 to form amide 6. The acylation is preferably carried out in an organic solvent (e.g., methylene chloride or DMF) at 0° to 80° C. in the presence of a tertiary amine, preferably DIPEA. Amide 6 is reacted with benzimidazole—amine 7 in a displacement reaction to produce compound 8. The displacement reaction is preferably carried out by shaking the reactants in DMF for an extended period, preferably 1–2 days. For compounds in which the $R^3$ group is not H, such compounds may be made by subjecting compound 8 to conventional reactions to add the $R^3$ substituent to form compound 9. For example, depending on the desired substituent, compound 8 may be reacted with a carboxylic acid, an acyl chloride, acyl anhydride, isocyanate, carbamoyl chloride, isothiocyanate, alkyl halide, alkyl sulfonate, or epoxide, or alternatively, compound 8 may be subjected to reductive alkylation with an aldehyde or ketone. Compound 10 is formed by cleavage from the linker and the resin portion of compound 9 by conventional means, e.g., by treating with dilute TFA in methylene chloride at ambient temperature for 10 to 60 minutes. If desired, compound 10 may be converted to a biolabile ester by standard esterification methods.

Compounds wherein q and r are both 0 may be prepared according to the solid phase synthesis shown in Scheme 2, below.

SCHEME 2

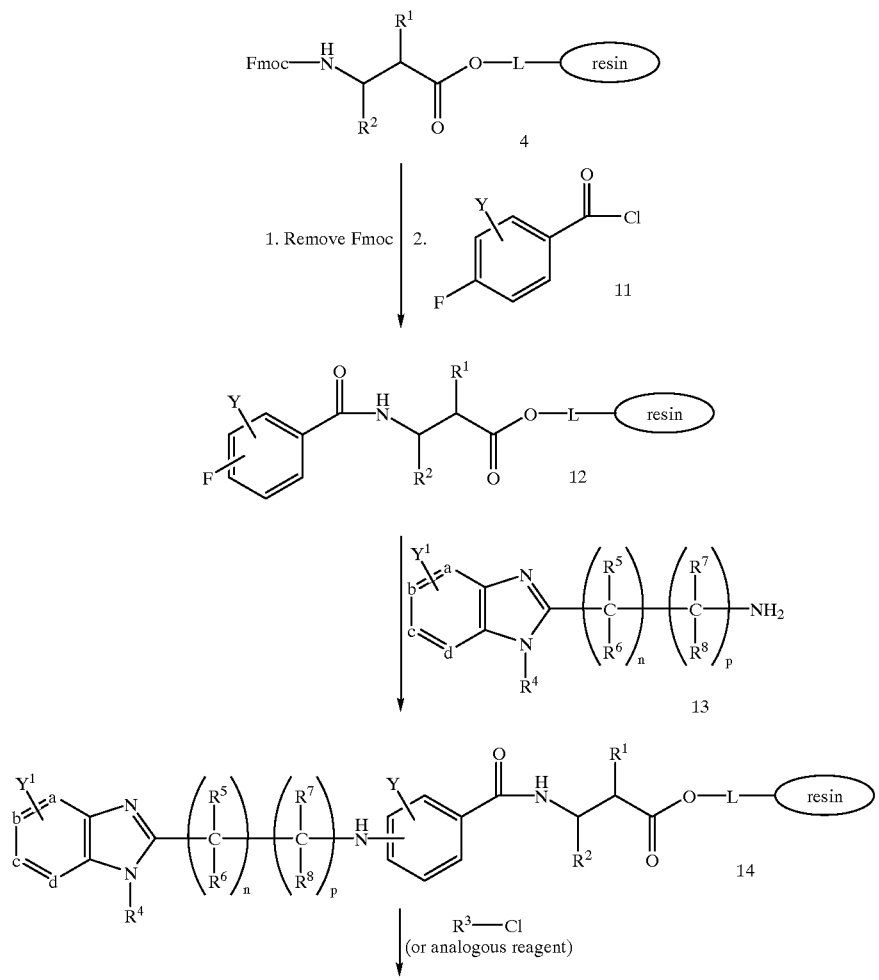

-continued

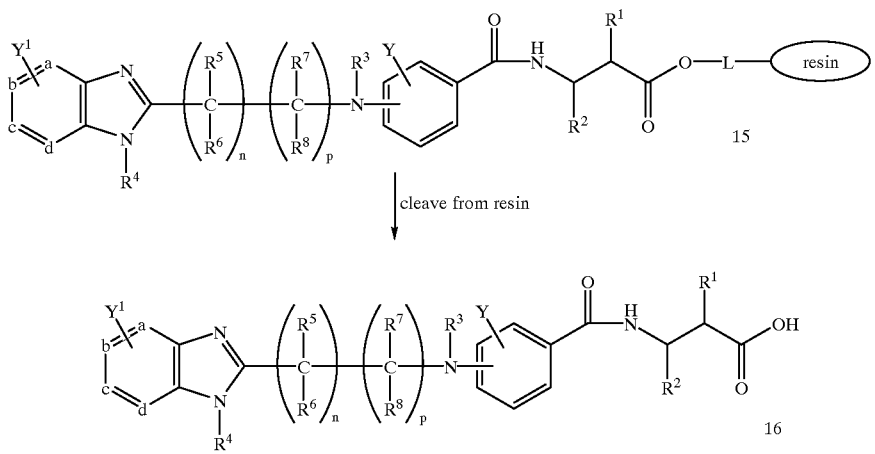

cleave from resin

In Scheme 2, compound 4, prepared as described in Scheme 1, is treated with piperidine in DMF at 0° to 80° C., and acylated with benzoyl chloride 11 to form amide 12. The acylation is preferably carried out in an organic solvent (e.g., methylene chloride or DMF) at 0° to 80° C. in the presence of a tertiary amine, preferably DIPEA. Amide 12 is subsequently reacted with a benzimidazole 13 to form compound 14, and if desired, reacted with a suitable reagent to add the $R^3$ group under the conditions described for Scheme 1 to form compound 15. Compound 16 is formed by cleavage from the linker and resin portion of compound 15 under the conditions described in Scheme 1. If desired, compound 16 may be converted to a biolabile ester by standard esterification methods. The starting compounds and reagents used in the foregoing schemes are either commercially available or may be prepared by methods well—known to those skilled in the art.

Those skilled in the art will recognize that reactive groups in the foregoing reaction schemes (e.g., carboxyl, amino, hydroxy) may be protected if desired or necessary with conventional protecting groups that can be subsequently removed by standard procedures. See, e.g., McOmie, Protecting groups In Organic Chemistry, Plenum Press, N.Y., 1973, and Greene and Wuts, Protecting Groups In Organic Synthesis, 2nd Ed., John Wiley & Sons, N.Y. 1991.

As an alternative to solid phase synthesis, the compounds of the present invention may be prepared by solution synthesis, employing appropriate protective groups for reactive groups. Particularly useful for carboxy protection are t—butyl esters, although other groups such as allyl and benzyl are also suitable. Intermediate esters may be converted to the acids by appropriate deprotection methods.

For preparing pharmaceutical compositions from the compounds of this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water—propylene glycol solutions for parenteral injection.

Liquid form preparations may also include solutions for intranasal administration.

Opthalmic preparations may be formulated using commercially available vehicles such as Sorbi-care® (Allergan) or Neodecadron® (Merck, Sharp & Dohme).

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from 0.01 mg to 1000 mg, more preferably from 0.1 mg to 200 mg, most preferably from 5 mg to 100 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention will be regulated according to the judgment of the attending clinician considering such factors as age, condition and size of the patient as well as severity of the symptoms being treated. A typical recommended dosage regimen is oral administration of from 0.02 mg to 4,000 mg/day, preferably 0.2 mg to 800 mg/day, most preferably 10 mg to 400 mg/day in two to four divided doses to block tumor growth.

The following examples illustrate the foregoing invention, although such examples should not be construed as limiting the scope of the invention. Alternative mechanistic pathways and analagous structures within the scope of the invention will be apparent to those skilled in the art.

EXAMPLES

In the Examples below, the "funnel apparatus" is a sintered glass funnel for agitating the contents with nitrogen and removal of the solvent by filtration. Where resins are "washed" with solvent, e.g., (20 mL×5), the resin in solvent (20 mL) is agitated for 2 minutes in a funnel apparatus, and solvent is removed by filtration (draining), and this sequence is repeated 4 additional times.

For the Examples below, "AA" refers to

L- 2,3-diaminopropionic acid on 2-chlorotrityl resin refers to

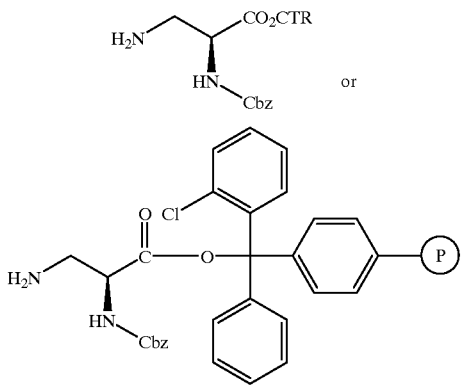

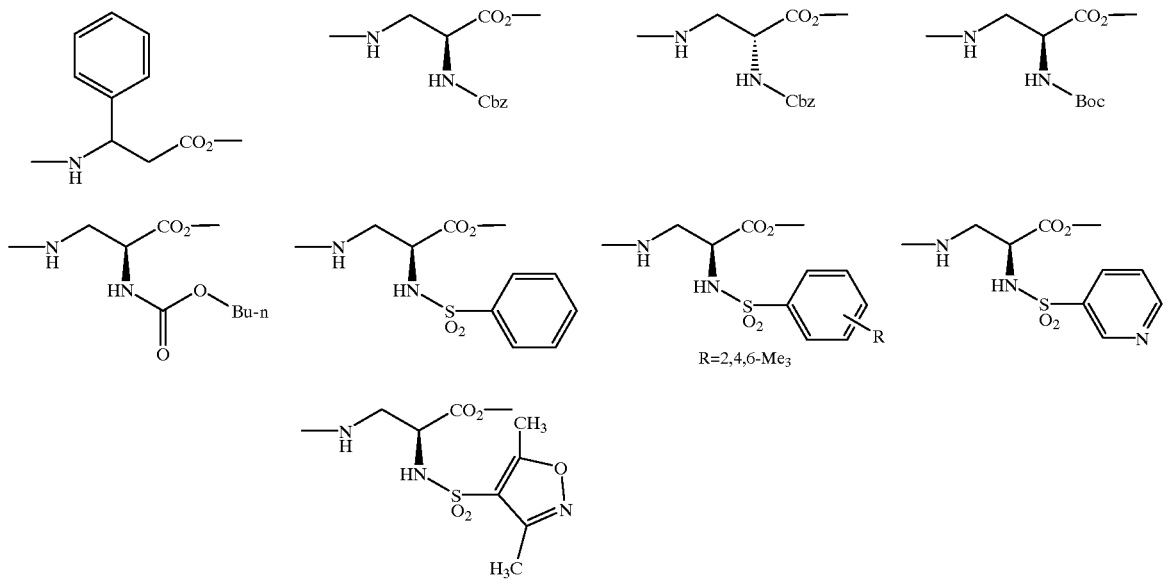

depending on the particular compounds used from the preparative examples. "—U—" refers to —$CH_2$—, —$CH_2$—$CH_2$—, or —$CH(CH_3)$—, depending on the particular compounds used from the preparative examples.

"2-chlorotrityl resin, chloride form" refers to

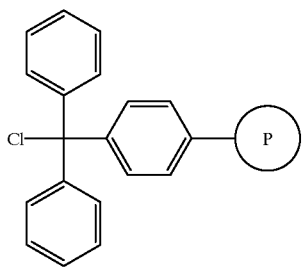

wherein (P) represents the resin (polymer) portion. "CTR" refers to 2-chlorotrityl resin. Thus, for example, $N^2$—Cbz—

Preparation 1

2-(Aminomethyl)benzimidazole

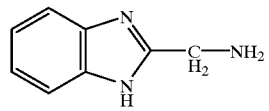

Add 2-(aminomethyl)benzimidazole, dihydrochloride, hydrate (18.50 g) to a solution of potassium hydroxide (9.50 g) in methanol (400 mL). Stir the resulting mixture at room temperature for 30 minutes, filter, and concentrate the filtrate in vacuo. Extract the residue with EtOAc (5×500 mL) and filter. Concentrate the filtrate in vacuo to give the title compound as a white solid (9.60 g).

Preparation 2

[3-[4-(Benzimidazol-2-ylmethyl)aminomethylbenzoyl]amino]-3-phenyl-propionic acid on 2-chlorotrityl resin

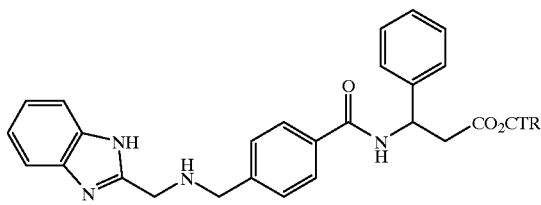

Step 1
3-Fmoc-amino-3-phenylpropionic acid

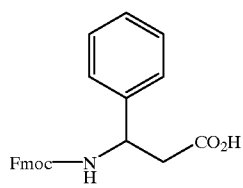

Combine 3-amino-3-phenylpropionic acid (3.70 g, 22.4 mmol) and NaHCO₃ (8.42 g, 100 mmol) in acetone (50 mL) and water (50 mL). Cool in an ice-bath. Add Fmoc-O-hydroxysuccinimide (9.40 g, 28.0 mmol), and stir the resulting mixture for 3 hours while the ice melts. Concentrate the mixture in vacuo, and extract the aqueous portion with EtOAc. Wash the EtOAc solution with 5% glacial acetic acid in water (3×300 mL), 5% NaHCO₃ solution (3×300 mL) and brine (3×300 mL). Concentrate the dried (MgSO₄) EtOAc solution in vacuo to give the title compound (contains Fmoc-O-hydroxysuccinimide) as a white foam which is used in Step 2.

Reference: W. M. Kazmierski, Int. J. Pep. Prot. Res., 45, 242 (1995).

Step 2
3-Amino-3-phenylpropionic acid on 2-chlorotrityl resin

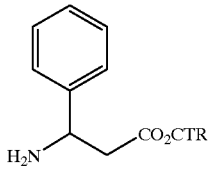

Step 2a
To a solution of DIPEA (1.6 mL) in DMF (10 mL), add the crude product (Preparation 2, Step 1) (0.64 g). Add 2-chlorotrityl resin, chloride form (2.00 g, 0.65 mmol/g). Agitate the resulting mixture for 30 minutes. Add MeOH (0.44 mL), agitate the mixture for 10 minutes, and drain. Wash the resin with DMF (30 mL×5) and then CH₂Cl₂ (30 mL×5) to give 3-Fmoc-amino-3-phenylpropionic acid on 2-chlorotrityl resin.

Step 2b
Wash the resin (Preparation 2, Step 2a) with DMF (20 mL×5). Add 20% piperidine in DMF (30 mL), agitate for 15 minutes, and collect the filtrate. Repeat two times. To determine loading level, combine filtrates in 100 mL volumetric flask, and add DMF to 100 mL (Solution A). Dilute Solution A (0.2 mL) to 100 mL in a volumetric flask. UV absorbance at 301 nM: 0.374

0.374×concentration/7800

0.374×20,000/7800=0.959 mmol/2 g (0.479 mmol/g)

Step 3
3-(4-Chloromethylbenzoyl)amino-3-phenylpropionic acid on 2-chlorotrityl resin

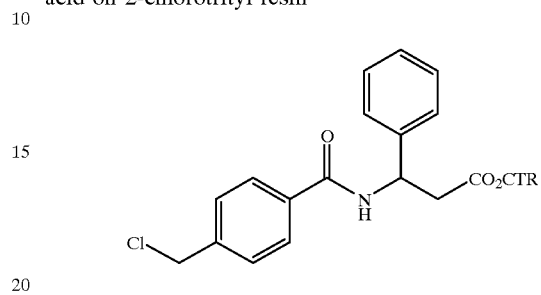

Place resin (Preparation 2, Step 2b) (2.00 g, 0.959 mmol) in CH₂Cl₂ (5 mL) in a vial, and treat with DIPEA (1.84 mL, 10.6 mmol), followed by 4-chloromethylbenzoylchloride (1.89 g, 9.6 mmol). Seal vial and place on a shaker for 2.5 hours. Transfer resin to funnel apparatus. Wash the resin with CH₂Cl₂ (20 mL×3), DMF (20 mL×3) and then CH₂Cl₂ (20 mL×3) to yield title resin.

Step 4
3-[4-(Benzimidazol-2-ylmethyl)aminomethylbenzoylamino-3-phenylpropionic acid on 2-chlorotrityl resin

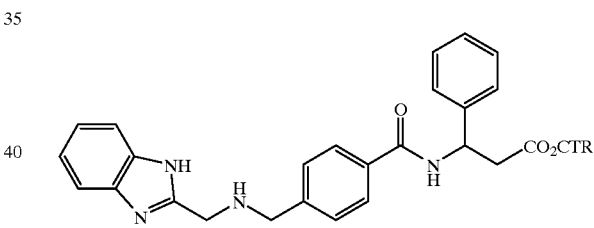

Shake the resin (Preparation 2, Step 3) (2.00 g, 0.479 mmol) and 2-(aminomethyl)benzimidazole (9.6 g) (Preparation 1) in DMF (25 mL) in a sealed vial for 44 hours. Transfer resin to funnel apparatus, and wash the resin with DMF (25 mL×5) and then CH₂Cl₂ (20 mL×5) to give the title resin.

Preparation 3

N³-[3-(Benzimidazol-2-ylmethyl)aminomethylbenzoyl]-N²-Cbz-L-2,3-diaminopropionic acid on 2-chlorotrityl resin

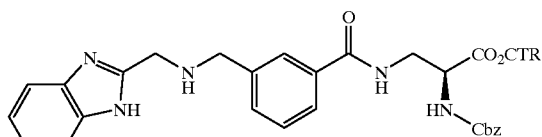

Step 1
N³-Fmoc-N²-Cbz-L-2,3-diaminopropionic acid

Combine N²-Cbz-L-2,3-diaminopropionic acid (2.66 g, 11.27 mmol) and NaHCO₃ (4.21 g, 50 mmol) in acetone (25 mL) and water (25 mL). Cool in an ice-bath. Add Fmoc-O-hydroxysuccinimide (4.70 g, 14.0 mmol), and stir the resulting mixture for 3 hours while the ice melts. Concentrate the mixture in vacuo, and extract the aqueous portion with EtOAc. Wash the EtOAc solution with 5% glacial acetic acid in water (3×125 mL), 5% NaHCO₃ solution (3×100 mL) and brine (3×100 mL). Concentrate the dried (MgSO₄) EtOAc solution in vacuo to give the title compound (contains Fmoc-O-hydroxysuccinimide) as a white foam (5.12 g) which is used in Step 2.

Reference: W. M. Kazmierski, Int. J. Pep. Prot. Res., 45, 242 (1995).

Step 2
N²-Cbz-L-2,3-diaminopropionic acid on 2-chlorotrityl resin

Step 2a
To a solution of DIPEA (1.47 mL) in DMF (30 mL), add the crude product of Preparation 3, Step 1 (1.5 g). Add 2-chlorotrityl resin, chloride form (2.0 g, 0.65 mmol/g). Agitate the resulting mixture for 30 minutes. Add MeOH (0.86 mL), and agitate the mixture for 10 minutes, and drain. Wash the resin with DMF (30 mL×5) and then CH₂Cl₂ (20 mL×5) to give N³-Fmoc-N²-Cbz-L-2,3-diaminopropionic acid on 2-chlorotrityl resin.

Step 2b
Wash the resin (Preparation 3, Step 2a) with DMF (20 mL×5). Add 20% piperidine in DMF (30 mL), agitate for 15 minutes, and collect the filtrate. Repeat two times. Determine the loading as in Preparation 2. Measure UV absorbance at 301 nM: 0.391

0.391×concentration/7800

0.391×20,000/7800=1.0026 mmol/2 g (0.501 mmol/g)

Step 3
N³-(3-Chloromethylbenzoyl)-N²-Cbz-L-2,3-diaminopropionic acid on 2-chlorotrityl resin Place resin (Preparation 3, Step 2b) (1.00 g, 0.50 mmol) in CH₂Cl₂ (5 mL) in a vial, and treat with DIPEA (0.96 g, 5.5 mmol), followed by 3-chloromethylbenzoyl chloride (0.95 g, 5 mmol). Seal vial and place on a shaker for 2.5 hours. Transfer resin to funnel apparatus. Wash the resin with CH₂Cl₂ (20 mL×3), DMF (20 mL×3) and then CH₂Cl₂ (20 mL×3) to yield title resin.

Step 4
N³-[3-(Benzimidazol-2-ylmethyl)aminomethylbenzoyl)-N²-Cbz-L-2,3-diaminopropionic acid on 2-chlorotrityl resin Shake the resin from Preparation 3, Step 3 (1.00 g, 0.5 mmol) and 2-(aminomethyl)benzimidazole (5 g) (Preparation 1) in DMF (25 mL) in a sealed vial for 44 hours. Transfer resin to funnel apparatus, and wash the resin with DMF (25 mL×5) and then CH₂Cl₂ (20 mL×3) to give the title resin.

Preparation 4

N³-[4-(Benzimidazol-2-ylmethyl)aminomethylbenzoyl)-N²-Cbz-L-2,3-diaminopropionic acid on 2-chlorotrityl resin Step 1
N³-(4-Chloromethylbenzoyl)-N²-Cbz-L-2,3-diaminopropionic acid on 2-chlorotrityl resin Place resin (Preparation 3, Step 2b) (1.00 g, 0.50 mmol) in CH₂Cl₂ (5 mL) in a vial, and treat with DIPEA (0.96 g, 5.5 mmol,) followed by 4-chloromethylbenzoyl chloride (0.95 g, 5 mmol). Seal vial and place on a shaker for 2.5 hours. Transfer resin to funnel apparatus. Wash the resin with CH₂Cl₂ (20 mL×3), DMF (20 mL×3) and then CH₂Cl₂ (20 mL×3) to yield title resin.

Step 2
N³-[4-(Benzimidazol-2-ylmethyl)aminomethylbenzoyl)-N²-Cbz-L-2,3-diaminopropionic acid on 2-chlorotrityl resin Shake the resin from Step 1 (1.0 g, 0.5 mmol) and 2-(aminomethyl)benzimidazole (5.00 g) (Preparation 1) in DMF (25 mL) in a sealed vial for 44 hours. Transfer resin to funnel apparatus, and wash the resin with DMF (25 mL×5) and then CH₂Cl₂ (20 mL×5) to give the title resin.

Preparation 5

N³-[4-(Benzimidazol-2-ylmethyl)
aminomethylbenzoyl]-N²-Cbz-D-2,3-
diaminopropionic acid on 2-chlorotrityl resin

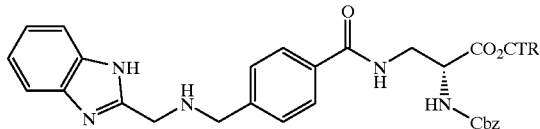

Step 1
N³-Fmoc-N²-Cbz-D-2,3-diaminopropionic acid

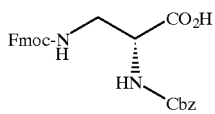

Combine N²-Cbz-D-2,3-diaminopropionic acid (1.3 g, 5.6 mmol) and NaHCO₃ (2.10 g, 25 mmol) in acetone (15 mL) and water (15 mL). Cool in an ice-bath. Add Fmoc-O-hydroxysuccinimide (2.35 g, 7.0 mmol), and stir the resulting mixture for 3 hours while the ice melts. Concentrate the mixture in vacuo, and extract the aqueous portion with EtOAc. Wash the EtOAc solution with 5% glacial acetic acid in water (3×60 mL), 5% NaHCO₃ solution (3×50 niL) and brine (3×50 mL). Concentrate the dried (MgSO₄) EtOAc solution in vacuo to give the title compound (contains Fmoc-O-hydroxysuccinimide) as a white foam which is used Step in 2.

Reference: W. M. Kazmierski, Int. J. Pep. Prot. Res., 45, 242 (1995).

Step 2
N²-Cbz-D-2,3-diaminopropionic acid on 2-chlorotrityl resin

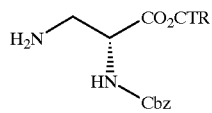

Step 2a
To a solution of DIPEA (0.8 mL) in DMF (10 mL), add the crude product from Preparation 5, Step 1 (0.81 g). Add 2-chlorotrityl resin, chloride form (1.00 g) ( 0.65 mmol/g). Agitate the resulting mixture for 30 minutes. Add MeOH (0.4 mL), and agitate the mixture for 10 minutes, and drain. Wash the resin with DMF (30 mL×5) and then CH₂Cl₂ (20 mL×5) to give N³-Fmoc-N²-Cbz-D-2,3-diaminopropionic acid on 2-chlorotrityl resin.

Step 2b
Wash the resin from Preparation 5, Step 2a with DMF (20 mL×5). Add 20% piperidine in DMF (30 mL), agitate for 15 minutes, and collect the filtrate. Repeat two times. Determine the loading as in Preparation 2. Measure UV absorbance at 301 nM: 0.154

0.154×concentration/7800

0.154×20,000/7800=0.394 mmol/ g

Step 3
N³-(4-Chloromethylbenzoyl)-N²-Cbz-D-2,3-diaminopropionic acid on 2-chlorotrityl resin

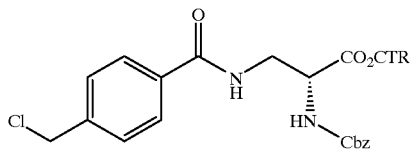

Place resin (Preparation 5, Step 2b) (1.00 g, 0.394 mmol) in CH₂Cl₂ (5 mL) in a vial, and treat with DIPEA (0.75 mL, 4.33 mmol) followed by 4-chloromethylbenzoyl chloride (0.75 g, 3.94 mmol). Seal vial and place on a shaker for 2.5 hours. Transfer resin to funnel apparatus. Wash the resin with CH₂Cl₂ (20 mL×3), DMF (20 mL×3) and then CH₂Cl₂ (20 mL×3) to yield title resin.

Step4
N³-[4-(Benzimidazol-2-ylmethyl)aminomethylbenzoyl)-N²-Cbz-D-2,3-diaminopropionic acid-2-chlorotrityl resin

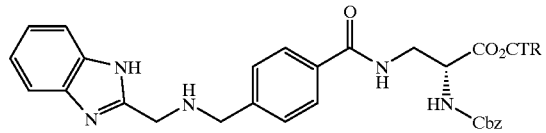

Shake the resin (Preparation 5, Step 3) (1.00 g, 0.394 mmol) and 2-(aminomethyl)benzimidazole (5.00 g) (Preparation 1) in DMF (25 mL) in a sealed vial for 44 hours. Transfer resin to funnel apparatus, and wash the resin with DMF (25 mL×5) and then CH₂Cl₂ (20 mL×5) to give the title resin.

Preparation 6

N³-[4-(Benzimidazol-2-ylmethyl)
aminomethylbenzoyl]-N²-Boc-L-2,3-
diaminopropionic acid on 2-chlorotrityl resin

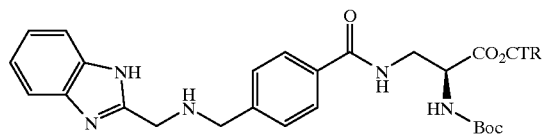

Step 1
N²-Boc-L-2,3-diaminopropionic acid on 2-chlorotrityl resin

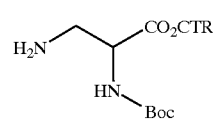

Step 1a
To a solution of DIPEA (1.60 mL) in DMF (10 mL), add (N³-Fmoc- N²-Boc-L-2,3-diaminopropionic acid) (0.72 g). Add the 2-chlorotrityl resin, chloride form (2.00 g) (0.65 mmol/g). Agitate the resulting mixture for 30 minutes. Add MeOH (0.8 mL), agitate the mixture for 10 minutes, and drain. Wash the resin with DMF (30 mL×5) and then CH₂Cl₂ (20 mL×5) to give N³-Fmoc-N²-Boc-L-2,3-diaminopropionic acid on 2-chlorotrityl resin.

Step 1b
Wash the resin (Preparation 6, Step 1) with DMF (20 mL×5). Add 20% piperidine in DMF (30 mL), agitate for 15 minutes, and collect the filtrate. Repeat two times. Determine the loading as in Preparation 2. Measure UV absorbance at 301 nM: 0.216

0.216×concentration/7800

0.216×20,000/7800=0.276 mmol/g

Step 2

N³-(4-Chloromethylbenzoyl)-N²-Boc-L-2,3-diaminopropionic acid on 2-chlorotrityl resin

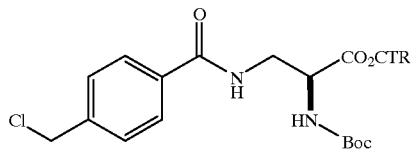

Place resin (Preparation 6, Step 1b) (2.00 g, 0.55 mmol) in CH₂Cl₂ (5 mL) in a vial, and treat with DIPEA (1.05 g, 6.08 mmol) followed by 4-chloromethylbenzoyl chloride (1.04 g, 5.52 mmol). Seal vial and place on a shaker for 2.5 hours. Transfer resin to funnel apparatus. Wash the resin with CH₂Cl₂ (20 mL×3), DMF (20 mL×3) and then CH₂Cl₂ (20 mL×3) to yield title resin.

Step 3

N³-[4-(Benzimidazol-2-ylmethyl)aminomethylbenzoyl)-N²-Boc-L-2,3-diaminopropionic acid on 2-chlorotrityl resin

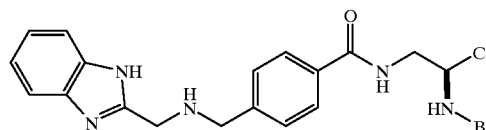

Shake the resin (Preparation 6, Step 2) (2.00 g, 0.55 mmol) and 2-(aminomethyl)benzimidazole (5.00 g) (Preparation 1) in DMF (25 mL) in a sealed vial for 44 hours. Transfer resin to funnel apparatus, and wash the resin with DMF (25 mL×5) and then CH₂Cl₂ (20 mL×5) to give the title resin.

Preparation 7

N³-[4-[2-(Benzimidazol-2-yl)ethyl]aminomethylbenzoyl)-N²-Cbz-L-2,3-diaminopropionic acid on 2-chlorotrityl resin

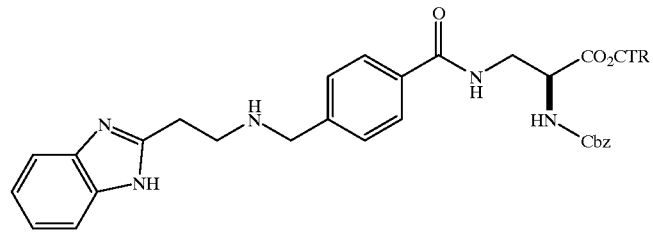

Step 1a.

2-[2-(Aminoethyl)]benzimidazole dihydrochloride

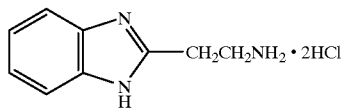

Combine o-phenylenediamine (10.8 g, 100 mmol) and β-alanine (13.4 g, 150 mmol) in 6 N HCl (100 mL). Heat at reflux 25 hours, allow to cool, and chill at −15° C. Filter the solid and wash with cold 6 N HCl, then cold EtOH. Dissolve the solid in 80% EtOH (125 mL), treat with decolorizing charcoal, and concentrate in vacuo to 40 g. Warm while adding EtOH (80 mL). Allow to cool, filter, and wash with EtOH to obtain the product as plates.

Step 1b

2-[2-(Aminoethyl)]benzimidazole

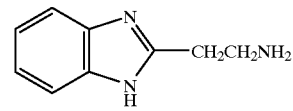

Add the product (Preparation 7, Step 1a) (7.18 g) to a solution of potassium hydroxide (3.45 g) in methanol (120 mL). Stir the resulting mixture at room temperature for 30 minutes, filter, and concentrate the filtrate in vacuo. Extract with EtOAc (3×500 mL) and filter. Concentrate the filtrate in vacuo to give the title compound as a white solid (3.33 g).

Step 2

N³-[4-[2-(Benzimidazol-2-yl)ethyl]aaminomethylbenzoyl)-N²-Cbz-L-2,3-diaminopropionic acid on 2-chlorotrityl resin

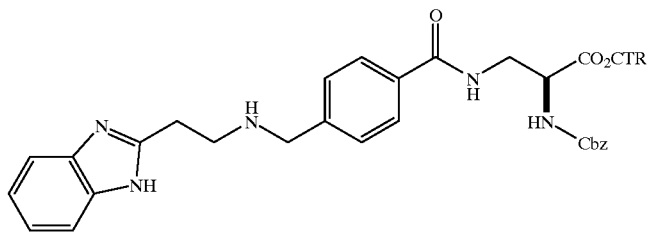

Shake the resin (Preparation 4, Step 1) (0.8 g, 0.4 mmol) and 2-[2-(aminoethyl)]benzimidazole (3.25 g) in DMF (25 mL) in a sealed vial for 44 hours. Transfer resin to funnel apparatus, and wash the resin with DMF (25 mL×5) and then $CH_2Cl_2$ (20 mL×5) to give the title resin.

Preparation 8

$N^3$-[4-[1-(Benzimidazol-2-yl)ethyl] aminomethylbenzoyl]-$N^2$-Cbz-L-2,3-diaminopropionic acid on 2-chlorotrityl resin

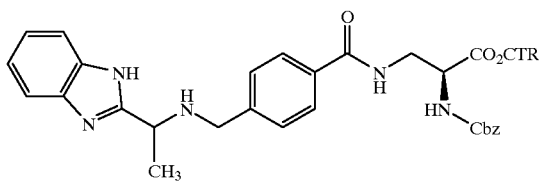

Step 1a.
2-(1-Aminoethyl)benzimidazole dihydrochloride hydrate

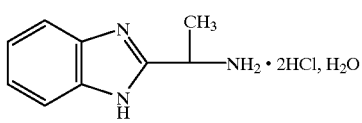

Combine o-phenylenediamine (10.8 g, 100 mmol) and d,l-alanine (13.4 g, 150 mmol) in 6 N HCl (100 mL) Heat at reflux 75 hours, allow to cool, and chill at −15° C. Filter to remove 2.4 g solid. Decolorize the filtrate with charcoal, concentrate in vacuo to 30 g, and dilute with 95% EtOH (90 mL). Chill at −15° C., filter and wash with cold 90% EtOH to obtain the title compound as a white powder.
Step 1b
2-(1-Aminoethyl)benzimidazole

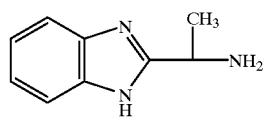

Add the product (Preparation 8, Step 1a) (6.99 g) to a solution of potassium hydroxide (3.36 g) in methanol (120 mL). Stir the resulting mixture at room temperature for 30 minutes, filter, and concentrate the filtrate in vacuo. Extract the residue with EtOAc (3×500 mL) and filter. Concentrate the filtrate in vacuo to give the title compound as a white solid (4.23 g).
Step 2
$N^3$-[4-[1 -(Benzimidazol-2-yl)ethyl] aminomethylbenzoyl]-$N^2$-Cbz-L-2,3-diaminopropionic acid on 2-chlorotrityl resin

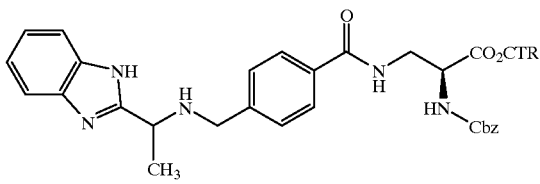

Shake the resin (Preparation 4, Step 1) (1.0 g, 0.5 mmol) and 2-(1-aminoethyl)benzimidazole (4.20 g) in DMF (25 mL) in a sealed vial for 44 hours. Transfer resin to funnel apparatus, and wash the resin with DMF (25 mL×5) and then $CH_2Cl_2$ (20 mL×5) to give the title resin.

Preparation 9

$N^3$-[4-[(Benzimidazol-2-yl)methyl] methylaminomethylbenzoyl)-$N^2$-Cbz-L-2,3-diaminopropionic acid on 2-chlorotrityl resin

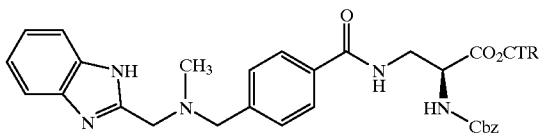

Step 1a 2-(Methylaminomethyl)benzimidazole dihydrochloride hydrate

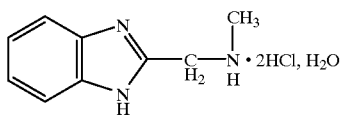

Combine o-phenylenediamine (10.8 g, 100 mmol) and sarcosine (13.4 g, 150 mmol) in 6 N HCl (100 mL). Heat at reflux 90 hours, allow to cool, and concentrate in vacuo to 45 g. Add EtOH (50 mL) and chill at −15° C. Filter the solid and wash with cold 90% EtOH. Dissolve in 80% EtOH (150 mL) and decolorize with charcoal. Concentrate in vacuo to 28 g, warm with 95% EtOH (160 mL), allow to cool, and filter to provide colorless rods.

Step 1b
2-(Methylaminomethyl)benzimidazole

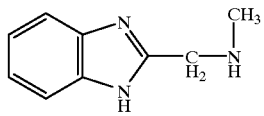

Add the product (Preparation 9, Step 1a) (2.33 g) to a solution of potassium hydroxide (1.21 g) in methanol (50 mL). Stir the resulting mixture at room temperature for 30 minutes, filter, and concentrate the filtrate in vacuo. Extract the with EtOAc (400 mL) and filter. Concentrate the filtrate in vacuo to give the title compound as a white solid (1.28 g).

Step 2
$N^3$-[4-[(Benzimidazol-2-yl)methyl]methylaminomethylbenzoyl]-$N^2$-Cbz-L-2,3-diaminopropionic acid on 2-chlorotrityl resin

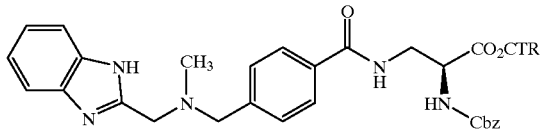

Shake the resin (Preparation 4, Step 1) (0.30 g, 0.15 mmol) and 2-(methylaminomethyl)benzimidazole (1.25 g) in DMF (20 mL) in a sealed vial for 44 hours. Transfer resin to funnel apparatus, and wash the resin with DMF (25 mL×5) and then $CH_2Cl_2$ (20 mL×5) to give the title resin.

Preparation 10

$N^3$-[4-(Benzimidazol-2-ylmethyl)aminomethylbenzoyl]-$N^2$-benzenesulfonyl-L-2,3-diaminopropionic acid on 2-chlorotrityl resin

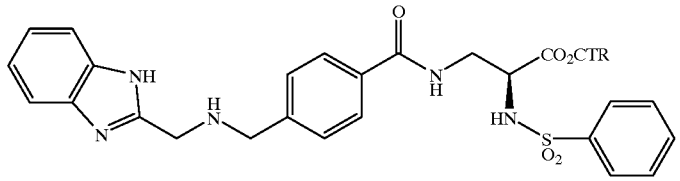

Step 1a
$N^2$-Benzenesulfonyl-L-Asparagine

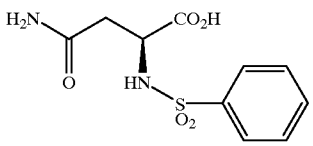

To L-Asparagine (10 g), add sodium hydroxide (3.4 g) and dioxane/water (50 mL/50 mL). Cool resulting solution in an ice bath and add benzenesulfonyl chloride (10.6 mL), sodium hydroxide (3.4 g), and water (80 mL). Stir for 3 hours. Add water (200 mL) and extract with EtOAc. Acidify the aqueous solution to pH 3 with concentrated HCl and cool to give a precipitate. After 1 hour collect the solid and dry it in vacuo at 40° C. to give the title compound.

Step 1b
$N^2$-Benzenesulfonyl-L-diaminopropionic acid

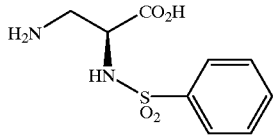

Prepare a solution of sodium hydroxide (10.5 g) in water (50 g), cool, and add bromine (2.5 mL). Add product from Step 1a (10 g) and sodium hydroxide (2.9 g) in water (35 mL) and stir for 30 minutes. Heat at 90° C. for 30 minutes and cool in an ice bath. Adjust to pH 7 with concentrated HCl. Collect the title compound as a white solid, mp 203–206° C. pos Step 1c $N^3$-Fmoc-$N^2$-benzenesulfonyl-L-2,3-diaminopropionic acid

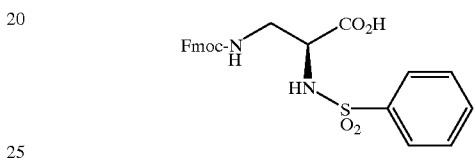

Combine $N^2$-benzenesulfonyl-L-2,3-diaminopropionic acid (2.92 g, 12.0 mmol) and $NaHCO^3$ (4.57 g) in acetone (40 mL) and water (40 mL). Cool in a ice-bath. Add Fmoc-O-hydroxysuccinimide (4.97 g, 19.2 mmol), and stir the resulting mixture for 3 hours while the ice melts. Add additional $NaHCO^3$ (1.5 g), acetone (40 mL) and water (40 mL), and dioxane (80 mL) and stir for 20 hours. Concentrate the mixture in vacuo, and extract the aqueous portion with EtOAc. Wash the EtOAc solution with 5% glacial acetic acid in water (3×300 mL), 5% $NaHCO_3$ solution (3×300 mL) and brine (3×300 mL). Concentrate the dried ($MgSO_4$) EtOAc solution in vacuo to give the title compound (contains Fmoc-O-hydroxysuccinimide) as a light yellow solid which is used in Step 2.

Reference: W. M. Kazmierski, Int. J. Pep. Prot. Res., 45, 242 (1995).

Step 2
$N^2$-Benzenesulfonyl-L-2,3-diaminopropionic acid on 2-chlorotrityl resin

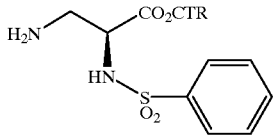

Step 2a
To a solution of DIPEA (1.60 mL) in DMF (10 mL), add ($N^3$-Fmoc- $N^2$-benzenesulfonyl-L-2,3-diaminopropionic acid) (0.787 g). Add the 2-chlorotrityl resin, chloride fonn (2.00 g) (0.65 mmol/g). Agitate the resulting mixture for 30 minutes. Add MeOH (0.8 mL), agitate the mixture for 10 minutes, and drain. Wash the resin with DMF (30 mL×5) and then CH$_2$Cl$_2$ (20 mL×5) to give N$^3$-Fmoc-N$^2$-benzenesulfonyl-L-2,3-diaminopropionic acid on 2-chlorotrityl resin.

Step 2b

Wash the resin (Preparation 10, Step 2a) with DMF (20mL×5). Add 20% piperidine in DMF (30 mL), agitate for 15 minutes, and collect the filtrate. Repeat two times. Determine the loading as in Preparation 1. Measure UV absorbance at 301 nM: 0.389

0.389×concentration/7800

0.389×20,000/7800=0.9958/2 g (0.498 mmol/ g)

Step 3

N$^3$-(4-Chloromethylbenzoyl)-N$^2$-benzenesulfonyl-L-2,3-diaminopropionic acid on 2-chlorotrityl resin

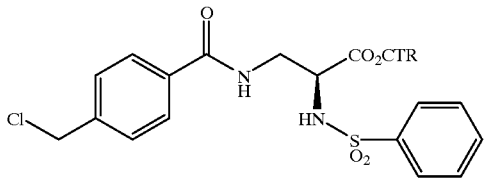

Place resin (Preparation 10, Step 2b) (1.00 g, 0.498 mmol) in CH$_2$Cl$_2$ (5 mL) in a vial, and treat with DIPEA (0.95 mL, 5.48 mmol) followed by 4-chloromethylbenzoyl chloride (0.94 g, 4.98 mmol). Seal vial and place on a shaker for 2.5 hours. Transfer resin to funnel apparatus. Wash the resin with CH$_2$Cl$_2$ (20 mL×3), DMF (20 mL×3) and then CH$_2$Cl$_2$ (20 mL×3) to yield title resin.

Step 4

N$^3$-[4-(Benzimidazol-2-ylmethyl)aminomethylbenzoyl)-N$^2$-benzenesulfonyl-L-2,3-diaminopropionic acid on 2-chlorotrityl resin

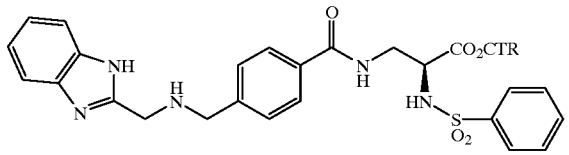

Shake the resin (Preparation 10, Step 3) (1.00 g, 0.55 mmol) and 2-(aminomethyl)benzimidazole (5.00 g) (Preparation 1) in DMF (25 mL) in a sealed vial for 44 hours. Transfer resin to funnel apparatus, and wash the resin with DMF (25 mL×5) and then CH$_2$Cl$_2$ (20 mL×5) to give the title resin.

Preparation 11

N$^3$-[4-(Benzimidazol-2-ylmethyl) aminomethylbenzoyl]-N$^2$-n-butoxycarbonyl-L-2,3-diaminopropionic acid on 2-chlorotrityl resin

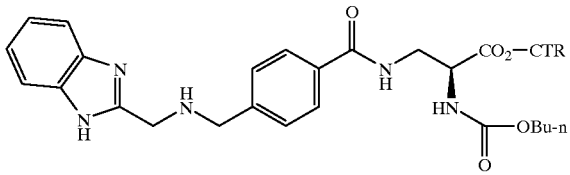

Step 1
N$^3$-Fmoc-N$^2$-n-butoxycarbonyl-L-2,3-diaminopropionic acid

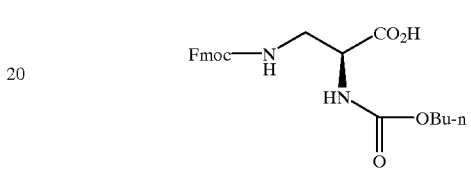

Combine N$^2$-n-butoxycarbonyl-L-2,3-diaminopropionic acid (18.0 g, 88.2 mmol) and NaHCO$_3$ (38.2 g) in acetone (400 mL) and water (400 mL). Cool in a ice-bath. Add Fmoc-O-hydroxysuccinimide (42.7 g, 126.6 mmol), and stir the resulting mixture for 3 hours while the ice melts. Continue stirring overnight for 20 hours. Concentrate the mixture in vacuo, and extract the aqueous portion with EtOAc. Wash the EtOAc solution with 5% glacial acetic acid in water (3×100 mL), 5% NaHCO$_3$ solution (8×100 mL) and brine (3×100 mL). Concentrate the dried (MgSO$_4$) EtOAc solution in vacuo. Chase with heptane, dry in vacuum oven overnight, and then transfer to a large dish and dry in a stream of air (to remove AcOH) to give the title compound (contains Fmoc-O-hydroxysuccinimide) as a light yellow solid which is used Step 2.

Reference: W. M. Kazmierski, Int. J. Pep. Prot. Res., 45, 242 (1995).
Step 2
N$^2$-n-Butoxycarbonyl-L-2,3-diaminopropionic acid on 2-chlorotrityl resin

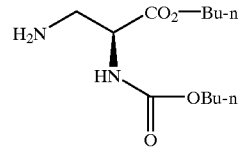

Step 2a
Add Dissolve (N$^3$-Fmoc- N$^2$-n-butoxycarbonyl-L-2,3-diaminopropionic acid) (16.7 g) in DMF (100 mL), warm, add DMF (50 mL), and filter. Add DIPEA (14 mL), and then add the 2-chlorotrityl resin, chloride form (15.00 g) (0.65 mmol/g). Agitate the resulting mixture for 45 minutes. Add MeOH, agitate the mixture for 10 minutes, and drain. Wash the resin with DMF (100 mL×5) and then CH$_2$Cl$_2$ (100 mL×5) to give N$^3$-Fmoc-N$^2$-n-butoxycarbonyl-L-2,3-diaminopropionic acid on 2-chlorotrityl resin.
Step 2b
Wash the resin (Preparation 11, Step 2a) with DMF (100 mL×5). Add 20% piperidine in DMF (100 mL), agitate for 15 minutes, and collect the filtrate. Repeat two times and Step 1a 1-Methyl-2-(aminomethyl)benzimidazole dihydrochloride

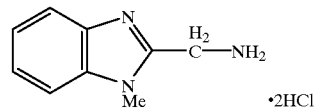

Combine N-methyl-o-phenylenediamine (12.2 g, 100 mmol) and glycine (11.3 g, 150 mmol) in 6 N HCl (100 mL). Heat at reflux 90 hours, allow to cool, and concentrate in vacuo to 60 g. Add EtOH (50 mL) and chill at −15° C. Filter the solid and wash with cold 90% EtOH. Dissolve the blue solid in water (30 mL), add EtOH (100 mL) and treat with decolorizing charcoal. Wash the solid with 2:1 EtOH-water and concentrate filtrates in vacuo to 33 g. Add water (15 mL) and warm while adding EtOH (150 mL). Allow to cool, filter, and wash with 90% EtOH to obtain the product as blue flakes. Process the filtrate to obtain a second crop.

Step 1b

1-Methyl-2-(aminomethyl)benzimidazole

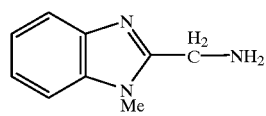

Add the product (Preparation 12, Step 1a) (10.3 g) to a solution of potassium hydroxide (5.20 g) in methanol (200 mL). Stir the resulting mixture at room temperature for 30 minutes, filter, and concentrate the filtrate in vacuo. Extract the with EtOAc (400 mL) and filter. Concentrate the filtrate in vacuo to give the title compound as a white solid (5.60 g).

Step 2

$N^3$-[4-[(1-Methylbenzimidazol-2-yl)methyl]aminomethylbenzoyl)-$N^2$-Cbz-L-2,3-diaminopropionic acid on 2-chlorotrityl resin

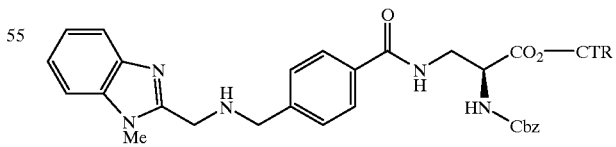

Shake the resin (Preparation 4, Step 1) (1.50 g, 0.60 mmol) and 1-methyl-2-(aminomethyl)benzimidazole (5.00 g) in DMF (25 mL) in a sealed vial for 18 hours. Transfer resin to funnel apparatus, and wash the resin with DMF (25 mL×5) and then CH$_2$Cl$_2$ (20 mL×5) to give the title resin.

then DMF (2×100 mL). Determine the loading as in Preparation 1 (dilute the filtrate to 1000 mL (solution A); take 1 mL and dilute to 100 mL) Measure UV absorbance at 301 nM: 0.794

0.794×concentration/7800

0.794×10,000/7800=10.18 mmol/15 g (0.67 mmol/ g)

Step 3

$N^3$-(4-Chloromethylbenzoyl)-$N^2$-n-butoxycarbonyl-L-2,3-diaminopropionic acid on 2-chlorotrityl resin

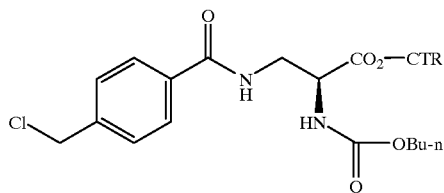

Place resin (Preparation 11, Step 2b) (15.00 g, 10 mmol) in CH$_2$Cl$_2$ (50 mL) in a vial, and treat with DIPEA (12.3 mL, 70 mmol) followed by 4-chloromethylbenzoyl chloride (11.5 g, 60 mmol). Gently sparge for 4 hours. Wash the resin with CH$_2$Cl$_2$ (100 mL×3), NMP (100 mL×3) and then CH$_2$Cl$_2$ (100 mL×5) to yield title resin.

Step 4

$N^3$-[4-(Benzimidazol-2-ylmethyl)aminomethylbenzoyl)-$N^2$-n-butoxycarbonyl-L-2,3-diaminopropionic acid on 2-chlorotrityl resin

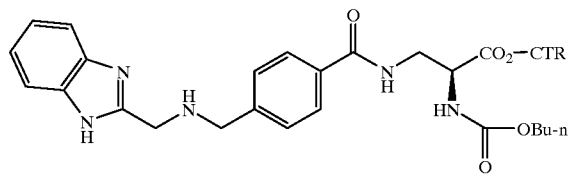

Shake the resin (Preparation 11, Step 3) (15.00 g, 10 mmol) and 2-(aminomethyl)benzimidazole (80.85 g) (Preparation 1) in NMP (500 mL) in a sealed vial for 24 hours. Transfer resin to funnel apparatus, and wash the resin with NMP (100 mL×3) and then CH$_2$Cl$_2$ (100 mL×5) to give the title resin.

Preparation 12

$N^3$-[4-[(1-Methylbenzimidazol-2-yl)methyl]aminomethylbenzoyl)-$N^2$-Cbz-L-2,3-diaminopropionic acid on 2-chlorotrityl resin

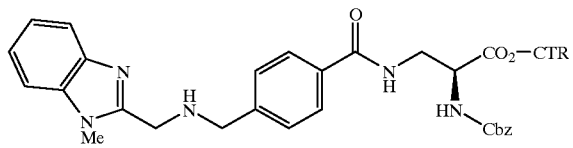

Preparation 13

N³-[4-[(5-Chlorobenzimidazol-2-yl)methy]laminomethylbenzoyl)-N²-Cbz-L-2,3-diaminopropionic acid on 2-chlorotrityl resin

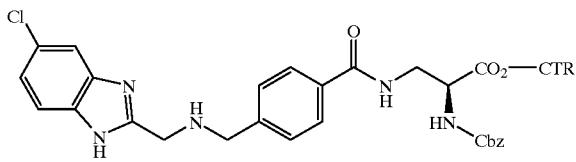

Step 1a
2-(aminomethyl)-5-chlorobenzimidazole dihydrochloride

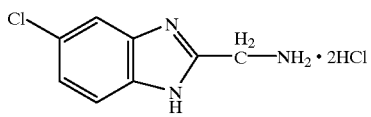

Combine 4-chloro-o-phenylenediamine (14.3 g, 100 mmmol) and glycine (11.3 g, 150 mmol) in 6 N HCl (100 mL). Heat at reflux 72 hours, allow to cool, add EtOH (30 mL), and chill at −15° C. Filter and wash with 3:10 EtOH-water, then water. Combine the filtrates, concentrate in vacuo to 50 g, and dilute with EtOH (75 mL). Chill at −15° C., filter and wash with cold 90% EtOH. Dry to obtain solid (18.8 g). Take up in 2:1 EtOH-water (120 mL), treat with decolorizing charcoal, concentrate in vacuo to 29 g, add water (6 mL), and heat while adding EtOH (120 mL). Boil to 100 mL, add EtOH (50 mL), boil to 125 mL, and allow to cool. Collect the solid and wash with 95% EtOH. Dry to obtain the title compound as a light orange powder.

Step 1b
2-(Aminomethyl)-5-chlorobenzimidazole

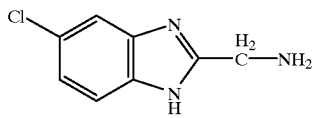

Add the product (Preparation 12, Step 1a) (10.3 g) to a solution of potassium hydroxide (5.20 g) in methanol (200 mL). Stir the resulting mixture at room temperature for 30 minutes, filter, and concentrate the filtrate in vacuo. Extract the with EtOAc (400 mL) and filter. Concentrate the filtrate in vacuo to give the title compound as a white solid (7.62 g).

Step 2
N³-[4-[(5-Chlorobenzimidazol-2-yl)methyl]aminomethylbenzoyl)-N²-Cbz-L-2,3-diaminopropionic acid on 2-chlorotrityl resin

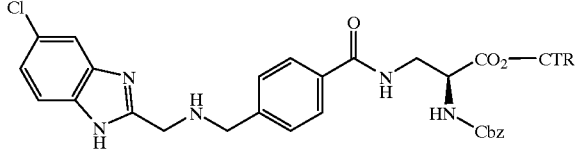

Shake the resin (Preparation 4, Step 1) (1.50 g, 0.60 mmol) and 1-methyl-2-inomethyl)benzimidazole (5.00 g) in DMF (25 mL) in a sealed vial for 18 hours. Transfer resin to funnel apparatus, and wash the resin with DMF (25 mL×5) and then CH₂Cl₂ (20 mL×5) to give the title resin.

Example 1

Acetylation of Products from Preparations 2–4 and 6–7

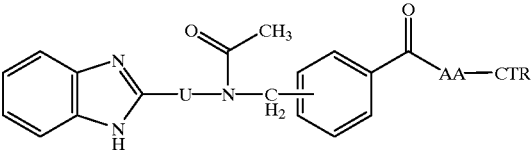

Place the resin (0.16 g, ≈0.07 mmol) in CH₂Cl₂ (4 mL) in a vial, and treat with DIPEA (0.77 mmol), followed by acetic anhydride (0.70 mmol). Seal the vial and place it on a shaker for 2 hours at room temperature. Place the resin in a funnel apparatus, and wash the resin with CH₂Cl₂ (15 mL×3), DMF (15 mL×5), and then CH₂Cl₂ (20 mL×5) to give a diacylated product. Wash the resin with DMF (15 ml×5), and then treat the resin with 20% piperidine in DMF (30 mL) with agitation for 1.5 hours. Wash the resin with DMF (15 mL×5) and then CH₂Cl₂ (20 mL×5) to yield monoacetylated resin.

Using the same method, prepare the following compound

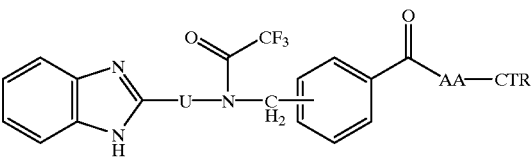

Example 2

Acylation of Products from Preparations 2–8 with Acid Chlorides and Chloroformates

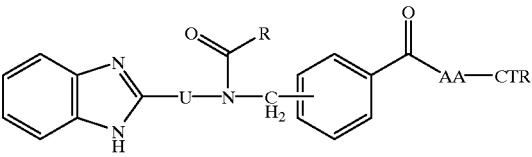

Place the resin (0.16 g, ≈0.07 mmol) in CH₂Cl₂ (4 mL) in a vial, and treat with DIPEA (0.77 mmol), followed by acid chloride or chloroformate (0.70 mmol). Seal the vial and place it on a shaker for 2 hours at room temperature. Place the resin in a funnel apparatus, and wash the resin with CH₂Cl₂ (15 mL×3), DMF (15 mL×5) and then CH₂Cl₂ (20 mL×5) to give a diacylated product. Wash the resin with DMF (15 ml×5), and then treat the resin with 20% piperidine in DMF (30 mL) with agitation for 1.5 hours. Wash the resin with DMF (15 mL×5) and then CH₂Cl₂ (20 mL×5) to yield monoacylated resin.

Acid chlorides and chloroformates used:

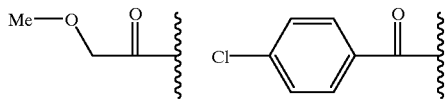

47

-continued

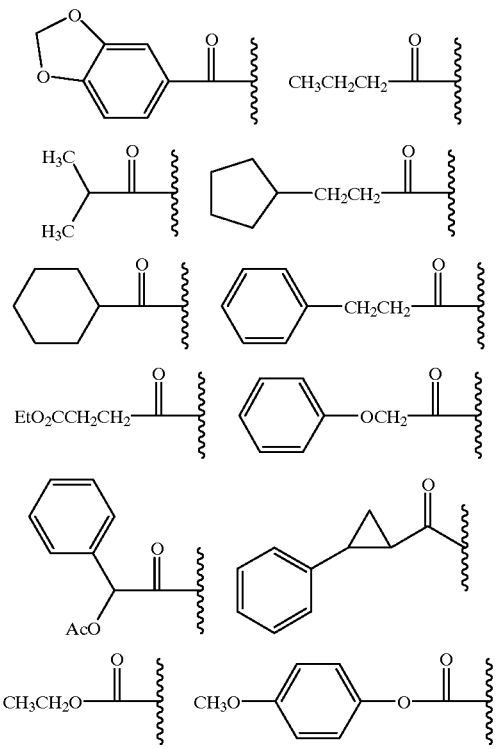

Example 3

Acylation of Products from Preparation 4 with Acids

Place the resin (0.16 g, ≈0.07 mmol) in CH$_2$Cl$_2$ (4 mL) in a vial, and treat with DIPEA (0.70 mmol) followed by carboxylic acid (0.35 mmol) and PyBroP (0.35 mmol). Seal the vial and place it on a shaker for 1.5 hours at room temperature. Place the resin in a funnel apparatus and wash the resin with CH$_2$Cl$_2$ (15 mL×3), DMF (15 mL×5), and then CH$_2$Cl$_2$ (20 mL×5) to give a diacylated product. Wash the resin with DMF (15 ml×5), and then treat the resin with 20% piperidine in DMF (30 mL) with agitation for 1.5 hours. Wash the resin with DMF (15 mL×5) and then CH$_2$Cl$_2$ (20 mL×5) to yield monoacylated resin.

Acids used:

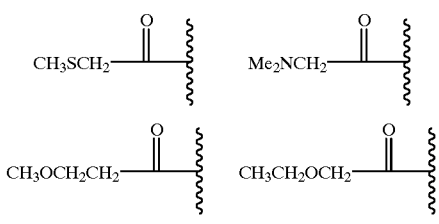

48

Example 4

Preparation of Ureas:

Reaction of Isocyanates or Isothiocyanates with Products from Preparation 4

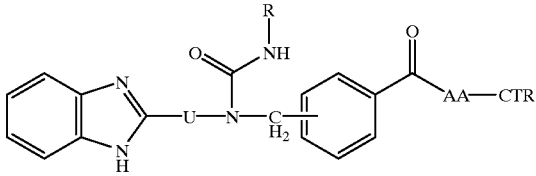

Place the resin (0.16 g, ≈0.107 mmol) in DMF (5 mL) in a vial and add isocyanate (0.22 mmol). Seal the vial and place it on a shaker for 2–2.5 hours at room temperature. Place the resin in a finnel apparatus and wash the resin with CH$_2$Cl$_2$ (15 mL×3), DMF (15 mL×5), and then CH$_2$Cl$_2$ (20 mL×5) to give the title resin.

Isocyanates used:

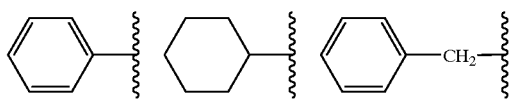

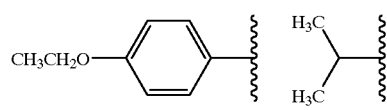

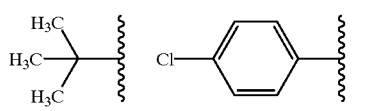

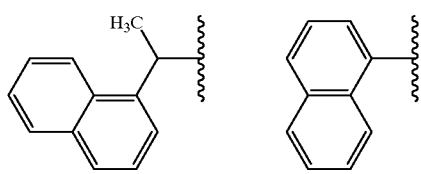

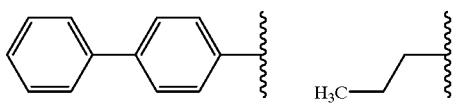

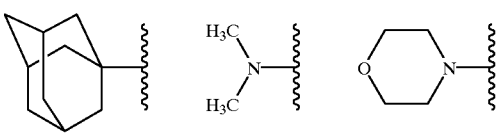

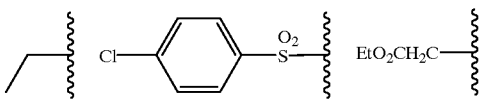

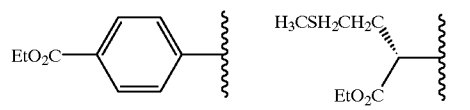

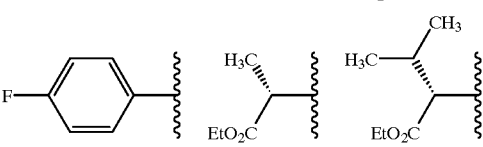

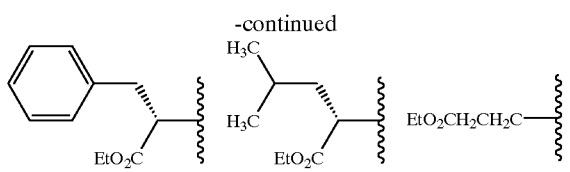

Isothiocyanate used:

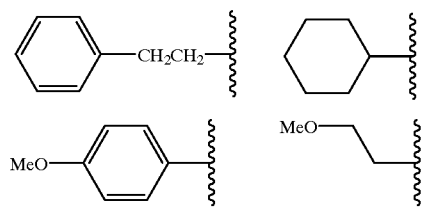

Example 5

Cleavage of Products from Resin

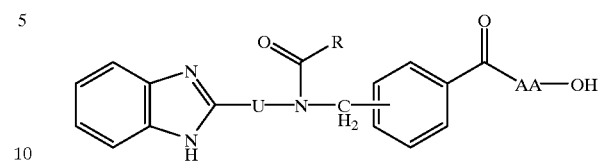

Treat the resins from Preparations 2–13 or Examples 1–4 (≈0.16 g) with $CH_2Cl_2$: $TFA$:$H_2O$ (99:0.95:0.05) (10 mL) at room temperature for 15 minutes and filter. Repeat this one time. Combine the filtrates, and concentrate on a Speed Vac. Add heptane (1 mL) and concentrate in Speed Vac. Dry the products in a vacuum oven at 40° C. for 20 hours to yield the following products listed in Tables 1 to 8, below (HPLC condition: Vydac column (218TP5405): 5–95% MeCN—$H_2O$ (0.1% TFA) gradient over 10 minutes, at 1 mL/min. UV detection 254 nM):

TABLE 1

| Example | Benxoyl Substituent | $R^3$ | MS m/e $[M + H]^+$ | HPLC Retention Time, min |
|---|---|---|---|---|
| 5-1 | para | H— | 502 | 3.91 |
| 5-2 | para | Cl-C6H4-C(O)- | 640 | 3.95 |
| 5-3 | para | Me-C(O)- | 544 | 4.13 |
| 5-4 | para | methylenedioxyphenyl-C(O)- | 650 | 5.45 |
| 5-5 | para | Me-O-CH2-C(O)- | 574 | 4.15 |
| 5-6 | meta | H— | 502 | 4.02 |

TABLE 1-continued

| Example | Benxoyl Substituent | R³ | MS m/e [M + H]⁺ | HPLC Retention Time, min |
|---|---|---|---|---|
| 5-7 | meta | 4-chlorobenzoyl | 640 | 6.10 |
| 5-8 | meta | acetyl | 544 | 4.24 |
| 5-9 | meta | 1,3-benzodioxole-5-carbonyl | 650 | 5.58 |
| 5-10 | meta | methoxyacetyl | 574 | 4.29 |

TABLE 2

| Example | R³ | MS m/e [M + H]⁺ | HPLC Retention Time, min |
|---|---|---|---|
| 5-11 | CH₃CH₂CH₂C(O)– | 572 | 5.84 |
| 5-12 | CF₃C(O)– | 598 | 5.99 |
| 5-13 | (CH₃)₂CHC(O)– | 572 | 5.77 |
| 5-14 | cyclopentyl-CH₂CH₂C(O)– | 626 | 6.85 |

TABLE 2-continued

| Example | R³ | MS m/e [M + H]⁺ | HPLC Retention Time, min |
|---|---|---|---|
| 5-15 | cyclohexyl-C(O)- | 612 | 6.43 |
| 5-16 | Ph-CH₂CH₂-C(O)- | 634 | 6.52 |
| 5-17 | EtO₂CCH₂CH₂-C(O)- | 630 | 6.36 |
| 5-18 | Ph-CH(OAc)-C(O)- | 678 | 6.33 |
| 5-19 | Ph-OCH₂-C(O)- | 636 | 5.77 |
| 5-20 | CH₃CH₂O-C(O)- | 574 | 6.43 |
| 5-21 | 4-CH₃O-C₆H₄-O-C(O)- | 652 | 6.57 |
| 5-22 | Ph-cyclopropyl-C(O)- | 646 | 6.58 |
| 5-23 | CH₃SCH₂-C(O)- | 589 | 5.68 |

TABLE 2-continued

| Example | R³ | MS m/e [M + H]⁺ | HPLC Retention Time, min |
|---|---|---|---|
| 5-24 | Me₂NCH₂-C(O)- | 587 | 4.92 |
| 5-25 | CH₃OCH₂CH₂-C(O)- | 588 | 5.49 |
| 5-26 | CH₃CH₂OCH₂-C(O)- | 588 | 5.50 |
| 5-27 | Ph-NH-C(O)- | 621 | 6.22 |
| 5-28 | Cyclohexyl-NH-C(O)- | 627 | 6.40 |
| 5-29 | PhCH₂-NH-C(O)- | 635 | 6.19 |
| 5-30 | iPr-NH-C(O)- | 585 | 5.72 |
| 5-31 | Ph-CH₂-CH₂-NH-C(S)- | 665 | 6.95 |
| 5-32 | 4-EtO-C₆H₄-NH-C(O)- | 665 | 6.46 |
| 5-33 | H₃C- | 516 | 5.33 |
| 5-34 | (H₃C)₃C-NH-C(O)- | 601 | 6.06 |

TABLE 2-continued
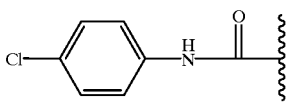
| Example | R³ | MS m/e [M + H]⁺ | HPLC Retention Time, min |
|---|---|---|---|
| 5-35 | 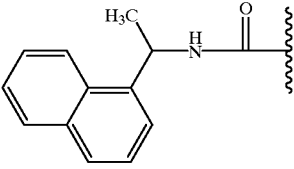 | 655 | 6.72 |
| 5-36 | 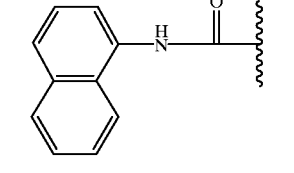 | 699 | 6.94 |
| 5-37 | 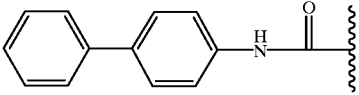 | 671 | 6.54 |
| 5-38 | 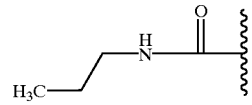 | 697 | 6.83 |
| 5-39 | 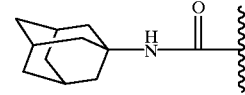 | 587 | 5.65 |
| 5-40 | 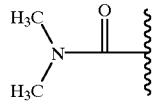 | 679 | 7.10 |
| 5-41 | 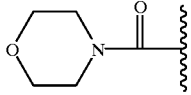 | 573 | 5.43 |
| 5-42* | 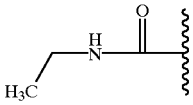 | 615 | 5.38 |
| 5-43 | 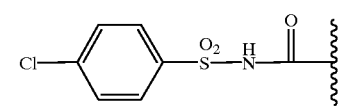 | 573 | 5.37 |
| 5-44 | | 719 | 6.49 |

TABLE 2-continued

| Example | R³ (structure) | MS m/e [M + H]⁺ | HPLC Retention Time, min |
|---|---|---|---|
| 5-45* | EtO₂CH₂C—NH—C(O)— | 631 | 5.57 |
| 5-46* | 4-MeO-C₆H₄—NH—C(S)— | 667 | 6.38 |
| 5-47* | 4-EtO₂C-C₆H₄—NH—C(O)— | 693 | 6.53 |
| 5-48* | H₃CSH₂CH₂C-CH(CO₂Et)—NH—C(O)— | 705 | 6.45 |
| 5-49* | 4-F-C₆H₄—NH—C(O)— | 639 | 6.31 |
| 5-50* | H₃C-CH(CO₂Et)—NH—C(O)— | 645 | 5.91 |
| 5-51* | (H₃C)₂CH-CH(CO₂Et)—NH—C(O)— | 673 | 6.46 |
| 5-52* | PhCH₂-CH(CO₂Et)—NH—C(O)— | 721 | 6.84 |
| 5-53* | (H₃C)₂CHCH₂-CH(CO₂Et)—NH—C(O)— | 687 | 6.77 |
| 5-54* | EtO₂CH₂CH₂C—NH—C(O)— | 645 | 5.78 |

TABLE 2-continued
| Example | R³ | MS m/e [M + H]⁺ | HPLC Retention Time, min |
|---|---|---|---|
| 5-55* | cyclohexyl-NH-C(=S)- | 643 | 6.93 |
| 5-56* | MeO-CH₂CH₂-NH-C(=S)- | 619 | 5.97 |
*Purified by Preparative TLC
TABLE 3
| Example | R³ | MS m/e [M + H]⁺ | HPLC Retention Time, min |
|---|---|---|---|
| 5-57 | H | 502 | 5.22 |
| 5-58 | CH₃OCH₂-C(=O)- | 574 | 5.30 |
| 5-59 | Ph-CH₂CH₂-C(=O)- | 634 | 6.50 |
TABLE 4
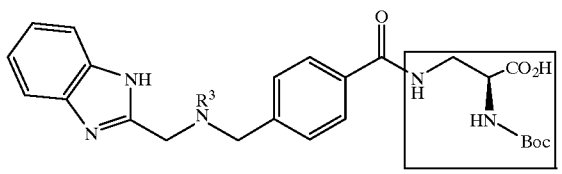
| Example | R³ | MS m/e [M + H]⁺ | HPLC Retention Time, min |
|---|---|---|---|
| 5-60 | H | 468 | 4.13 |

TABLE 4-continued
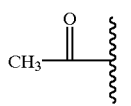
| Example | R³ | MS m/e [M + H]⁺ | HPLC Retention Time, min |
|---|---|---|---|
| 5-61 | 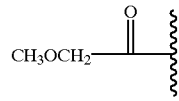 | 510 | 4.84 |
| 5-62 | 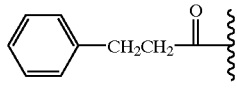 | 540 | 4.85 |
| 5-63 | 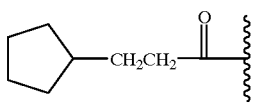 | 600 | 6.29 |
| 5-64 | 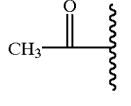 | 592 | 6.64 |
TABLE 5
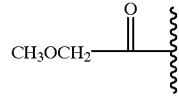
| Example | R³ | MS m/e [M + H]⁺ | HPLC Retention Time, min |
|---|---|---|---|
| 5-65 | H | 429 | 4.19 |
| 5-66 | 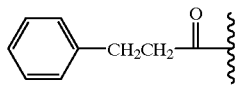 | 471 | 4.93 |
| 5-67 | 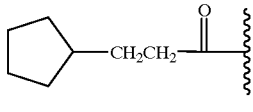 | 501 | 4.91 |
| 5-68 | | 561 | 6.32 |
| 5-69 | | 553 | 6.69 |

TABLE 6
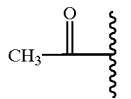
| Example | R³ | MS m/e [M + H]⁺ | HPLC Retention Time, min |
|---------|-----|-----------------|--------------------------|
| 5-70 | H | 516 | 4.94 |
| 5-71 | 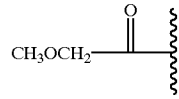 | 558 | 5.25 |
| 5-72 | 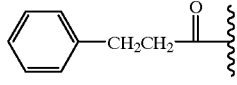 | 588 | 5.30 |
| 5-73 | 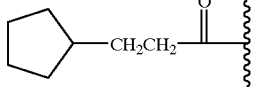 | 648 | 6.50 |
| 5-74 | 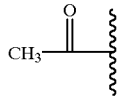 | 640 | 6.78 |
TABLE 7
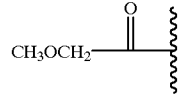
| Example | R³ | MS m/e [M + H]⁺ | HPLC Retention Time, min |
|---------|-----|-----------------|--------------------------|
| 5-75 | H | 516 | 5.36 |
| 5-76 | 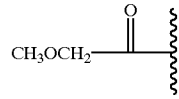 | 558 | 5.23 |
| 5-77 | 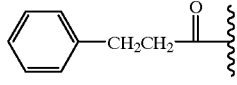 | 588 | 5.24 |
| 5-78 | 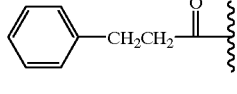 | 648 | 6.52 |

TABLE 7-continued

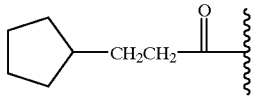

| Example | R³ | MS m/e [M + H]⁺ | HPLC Retention Time, min |
|---|---|---|---|
| 5-79 | cyclopentyl-CH₂CH₂-C(O)- | 640 | 6.84 |

TABLE 8

| Example | R³ | MS m/e [M + H]⁺ | HPLC Retention Time, min |
|---|---|---|---|
| 5-80* | CH₃OCH₂-C(O)- | 579 | 5.3 |
| 5-81* | cyclohexyl-NH-C(O)- | 632 | 6.23 |

*Purified by Preparative TLC

TABLE 8-1

| Example | R³ | MS m/e [M + H]⁺ | HPLC Retention Time, min |
|---|---|---|---|
| 5-82* | cyclohexyl-NH-C(O)- | 593 | 6.17 |

TABLE 8-1-continued

| Example | R³ | MS m/e [M + H]⁺ | HPLC Retention Time, min |
|---|---|---|---|
| 5-83* | phenyl-NH-C(O)- | 587 | 6.01 |
| 5-84* | isopropyl-NH-C(O)- | 553 | 5.45 |
| 5-85* | (CH₃)₃C-NH-C(O)- | 567 | 5.91 |
| 5-86* | EtO₂CH₂C-NH-C(O)- | 597 | 5.54 |
| 5-87* | H₃CSH₂CH₂C(EtO₂C)-NH-C(O)- | 671 | 6.25 |

TABLE 8-1-continued

| Example | R³ | MS m/e [M + H]⁺ | HPLC Retention Time, min |
|---|---|---|---|
| 5-88* | 4-F-C₆H₄-NH-C(O)-CH₂- | 605 | 6.16 |
| 5-89* | (S)-CH₃CH(CO₂Et)-NH-C(O)-CH₂- | 611 | 5.74 |
| 5-90* | (CH₃)₂CH-CH(CO₂Et)-NH-C(O)-CH₂- | 639 | 6.30 |
| 5-91* | 4-EtO₂C-C₆H₄-NH-C(O)-CH₂- | 659 | 6.46 |

*Purified by Preparative TLC

TABLE 8-2

| Example | R³ | MS m/e [M + H]⁺ | HPLC Retention Time, min |
|---|---|---|---|
| 5-92* | cyclohexyl-NH-C(O)-CH₂- | 641 | 6.32 |
| 5-93* | iPr-NH-C(O)-CH₂- | 601 | 5.67 |

*Purified by Preparative TLC

TABLE 8-3

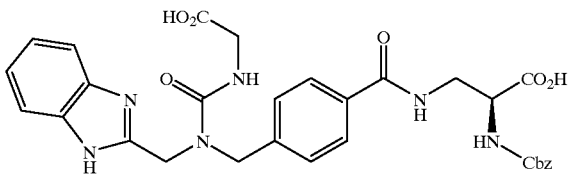

| Example | R³ | MS m/e [M + H]⁺ | HPLC Retention Time, min |
|---|---|---|---|
| 5-94* | cyclohexyl-NH-C(O)-CH₂- | 661 | 6.69 |
| 5-95* | iPr-NH-C(O)-CH₂- | 621 | 5.98 |

*Purified by Preparative TLC

Example 6

N³-[4-[(Benzimidazol-2-yl)methyl]
[[(carboxymethyl)amino]carbonyl]
aminomethylbenzoyl]-N²-Cbz-L-2,3-
diaminopropionic acid Dissolve N³-[4-[(benzimidazol-2-yl)methyl]
[[(ethoxycarbonylmethyl)amino]-carbonyl]
aminomethylbenzoyl]-N²-Cbz-L-2,3-diaminopropionic acid
(5–45) (2.60 g, 4.1 mmol) in MeOH (12 mL) and slowly add
1 N NaOH (40 mL). After 3 hours, slowly add 1 N HCl (40
mL) and then add 1 N HCl to pH 6.5 to give a white
precipitate. Decant water and wash with water (2×10 mL).
Dry title compound (Table 8–4) in vacuum oven.

Example 7

N³-[4-[(Benzimidazol-2-yl)methyl]
[[(carboxymethyl)amino]carbonyl]
aminomethylbenzoyl]-N²-(n-butoxycarbonyl)-L-2,3-
diaminopropionic acid

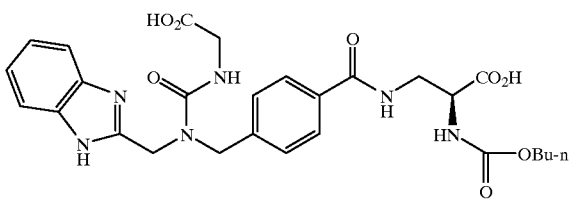

Dissolve N³-[4-[(benzimnidazol-2-yl)methyl]
[[(ethoxycarbonylmethyl)amino]-carbonyl]

aminomethylbenzoyl]-N²-(n-butoxycarbonyl)-L-2,3-diaminopropionic acid (5–86) (0.432 g, 0.72 mmol) in MeOH (5 mL) and slowly add 1 N NaOH (4 mL). After 3 hours, evaporate the MeOH under a steam of nitrogen. Slowly add 1 N HCl (4 mL) and then add 1 N HCl to pH 6.5 to give a white gum. Decant water dry title compound (Table 8-4) in vacuum oven.

TABLE 8-4

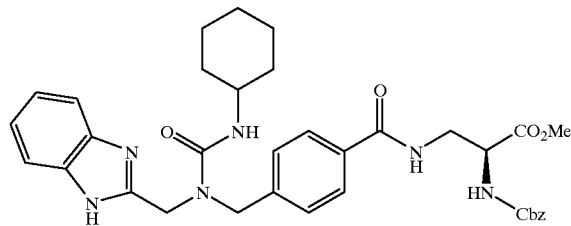

| Example | Q | MS m/e [M + H]⁺ | HPLC Retention Time, min |
|---|---|---|---|
| 5-96 | Cbz | 603 | 5.22 |
| 5-97 | n-BuO₂C | 569 | 4.98 |

Example 8

Methyl N³-[4-[(Benzimidazol-2-yl)methyl] [[(cyclohexyl)amino]carbonyl] aminomethylbenzoyl]-N²-(n-butoxycarbonyl)-L-2,3-diaminopropionate Add 3 M HCl in MeOH (5 mL) to N³-[4-[(benzimidazol-2-yl)methyl][[(cyclohexyl)amino]carbonyl]amino-methylbenzoyl]-N²-(n-butoxycarbonyl)-L-2,3-diaminopropionic acid (0.155 g) in MeOH (20 mL) and heat under reflux for 7 hours. The reaction mixture was concentrated in vacuo. MeOH was added and concentrated in vacuo to give the title compound as a white solid. MS m/e [M+H] 641: HPLC retention time: 6.77 min.

The following assay procedure, which is a competition radioligand binding assay, was carried out to determine the activity of the foregoing compounds as $\alpha_v\beta_3$ antagonists. The competitive assay procedure described in Kumar, et. al., "Biochemical Characterization Of The Binding Of Echistatin To Integrin $\alpha_v\beta_3$ Receptor", Journal Of Pharmacology And Experimental Therapeutics, Vol. 283, No. 2, pp. 843–853 (1997) was employed. Thus, binding of ¹²⁵I-echistatin (radiolabeled by the chloramine-T method to a specific activity of 2000 Ci/mmol (Amersham, Chicago, Ill.)) to $\alpha_v\beta_3$ receptor (purified from human placenta), both prepared as described in Kumar, et al., was competed by the compounds prepared in the foregoing examples. Purified $\alpha_v\beta_3$ receptor was coated onto Microlite-2 plates at a concentration of 50 ng/well. ¹²⁵I-echistatin was added to the wells to a final concentration of 0.05 nM in binding buffer (50 μl/well) in the presence of the competing test compound. The competing test compounds were employed at serially diluted concentrations ranging from 1 pM to 100 nM. After a 3 hour incubation at room temperature, the wells were washed, and radioactivity, reflecting binding by ¹²⁵I-echistatin to $\alpha_v\beta_3$ receptors, was determined with Top Count (Packard). Each data point is an average of values from triplicate wells.

Specific binding of ¹²⁵I-echistatin was calculated as the difference between the amount of ¹²⁵I-echistatin bound in the absence (total binding) and the amount of ¹²⁵I-echistatin bound in the presence of a 200-fold molar excess of unlabeled echistatin (non-specific binding). The efficacy of the test compounds for inhibiting specific binding of ¹²⁵I-echistatin to $\alpha_v\beta_3$ receptors was determined by plotting a graph of specific binding (y-axis) as a function of test compound concentration (x-axis). The concentration of test compound required to inhibit 50% of the specific binding (IC₅₀) was determined from the plot. The IC₅₀ may be directly converted mathematically to Ki, which is a measure of the receptor binding affinity of the compounds under the defined assay conditions.

To measure the relative affinity of the test compounds for $\alpha_v\beta_3$ receptors versus affinity for $\alpha_{IIb}\beta_3$ receptors, similar competitive assays were carried out using purified $\alpha_{IIb}\beta_3$ receptor and ¹²⁵I-echistatin (iodinated using the lactoperoxidase method). The specificity index, which is a measure of the relative binding affinity for $\alpha_v\beta_3$ versus $\alpha_{IIb}\beta_3$, may be determined by dividing the IC₅₀ value for $\alpha_{IIb}\beta_3$ by the IC₅₀ value for $\alpha_v\beta_3$.

The $\alpha_v\beta_3$ IC₅₀ values determined by the foregoing assay for the compounds identified in the preceding examples, and the specificity index (IC₅₀ $\alpha_{IIb}\beta_3$/IC₅₀ $\alpha_v\beta_3$) are summarized in the tables below.

TABLE 9

| Example | IC50, nM |
|---|---|
| 5-1 | 5.4 |
| 5-2 | 6.5 |
| 5-3 | 1.9 |
| 5-4 | 2.9 |
| 5-5 | 0.42 |
| 5-6 | ~500 |
| 5-7 | ~500 |
| 5-8 | ~500 |
| 5-9 | ~500 |
| 5-10 | ~500 |

TABLE 10

| Example | IC50, nM | SPECIFICITY $\alpha_{IIb}\beta_3/\alpha v\beta 3$ |
|---|---|---|
| 5-11 | 3.4 | 70 |
| 5-12 | 5.6 | 87 |
| 5-13 | 3.1 | 38 |
| 5-14 | 5.8 | 117 |
| 5-15 | 4.3 | 95 |
| 5-16 | 4.4 | 899 |
| 5-17 | 4.6 | 76 |
| 5-18 | 4.4 | 82 |
| 5-19 | 8.9 | 34 |
| 5-20 | 7.2 | 15 |
| 5-21 | 4.4 | 41 |
| 5-22 | 6.4 | 26 |
| 5-23 | 5.5 | 22 |
| 5-24 | 5.3 | 14 |
| 5-25 | 4.5 | 52 |
| 5-26 | 3.5 | 91 |
| 5-27 | 1.56 | 481 |
| 5-28 | 0.65 | 1136 |

TABLE 10-continued

| Example | IC50, nM | SPECIFICITY $\alpha_{IIb}\beta_3/\alpha v\beta 3$ |
|---|---|---|
| 5-29 | 4.3 | 144 |
| 5-30 | 2.3 | 296 |
| 5-31 | 6.0 | 80 |
| 5-32 | 6.5 | 151 |
| 5-33 | 17 | 128 |
| 5-34 | 2.3 | 421 |
| 5-35 | 8.1 | 240 |
| 5-36 | 11.7 | 129 |
| 5-37 | 5.3 | 203 |
| 5-38 | 13.6 | 49 |
| 5-139 | 3.1 | 223 |
| 5-40 | 5.7 | 288 |
| 5-41 | 2.8 | 19 |
| 5-42 | 1.8 | 39 |
| 5-43 | 2.2 | 585 |
| 5-44 | 19.6 | 66.3 |
| 5-45 | 2.2 | 1333 |
| 5-46 | 2.7 | 1065 |
| 5-47 | 2.2 | 1252 |
| 5-48 | 1.0 | 2028 |
| 5-49 | 4.2 | 504 |
| 5-50 | 3.0 | 805 |
| 5-51 | 1.1 | 1210 |
| 5-52 | 4.0 | 448 |
| 5-53 | 3.8 | 483 |
| 5-54 | 2.0 | 413 |
| 5-55 | 2.5 | 620 |
| 5-56 | 1.6 | 514 |

TABLE 11

| Example | IC50, nM | Specificity $\alpha_{IIb}\beta_3/\alpha v\beta 3$ |
|---|---|---|
| 5-57 | 1293 | 1.43 |
| 5-58 | 118 | 46 |
| 5-59 | 129 | 65 |

TABLE 12

| Example | IC50, nM | Specificity $\alpha_{IIb}\beta_3/\alpha v\beta 3$ |
|---|---|---|
| 5-60 | 25 | 90 |
| 5-61 | 17 | 324 |
| 5-62 | 30 | 419 |
| 5-63 | 20 | 293 |
| 5-64 | 16 | 499 |

TABLE 13

| Example | IC50, nM | Specificity $\alpha_{IIb}\beta_3/\alpha v\beta 3$ |
|---|---|---|
| 5-65 | 9,227 | 0.4 |
| 5-66 | 9,468 | 0.4 |
| 5-67 | 7,373 | 0.5 |
| 5-68 | 6,630 | 0.4 |
| 5-69 | 10,514 | 0.4 |

TABLE 14

| Example | IC50 nM | Specificity $\alpha_{IIb}\beta_3/\alpha v\beta 3$ |
|---|---|---|
| 5-70 | 413 | 0.2 |
| 5-71 | 266 | 0.3 |

TABLE 14-continued

| Example | IC50 nM | Specificity $\alpha_{IIb}\beta_3/\alpha v\beta 3$ |
|---|---|---|
| 5-72 | 559 | 0.5 |
| 5-73 | 170 | 0.7 |
| 5-74 | 238 | 0.6 |

TABLE 15

| Example | IC50, nM | Specificity $\alpha_{IIb}\beta_3/\alpha v\beta 3$ |
|---|---|---|
| 5-75 | 306 | 10.2 |
| 5-76 | 50 | 6.7 |
| 5-77 | 49 | 12.4 |
| 5-78 | 21 | 33.9 |
| 5-79 | 33 | 19.0 |

TABLE 16

| Example | IC50, nM | Specificity $\alpha_{IIb}\beta_3/\alpha v\beta 3$ |
|---|---|---|
| 5-80 | 4.4 | 11 |
| 5-81 | 8.2 | 8.0 |
| 5-82 | 2.2 | 1259 |
| 5-83 | 1.8 | 1689 |
| 5-84 | 3.6 | 712 |
| 5-85 | 1.8 | 1223 |
| 5-86 | 3.3 | 793 |
| 5-87 | 2.0 | 1569 |
| 5-88 | 2.0 | 1657 |
| 5-89 | 3.3 | 1094 |
| 5-90 | 2.6 | 1697 |
| 5-91 | 2.8 | 1183 |
| 5-92 | 7.6 | 174 |
| 5-93 | 6.7 | 124 |
| 5-94 | 3.8 | 399 |
| 5-95 | 1.7 | 775 |
| 5-96 | 3.4 | 528 |
| 5-97 | 4.3 | 2600 |

Pharmaceutical Dosage Form Examples

The following are examples of pharmaceutical dosage forms which contain a compound (i.e., "active compound") of the invention. The scope of the invention in its pharmaceutical composition aspect is not to be limited by the examples provided.

Example 9

Tablets

Tablets

| No. | Ingredients | mg/tablet | mg/tablet |
|---|---|---|---|
| 1. | Active compound | 100 | 5 |
| 2. | Lactose USP | 122 | 40 |
| 3. | Corn Starch, Food Grade, as a 10% paste in Purified Water | 30 | 25 |
| 4. | Corn Starch, Food Grade | 45 | 25 |
| 5. | Magnesium Stearate | 3 | 5 |
| | Total | 300 | 100 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example 10

Capsules

| | Capsules | | |
|---|---|---|---|
| No. | Ingredient | mg/capsule | mg/capsule |
| 1. | Active compound | 100 | 5 |
| 2. | Lactose USP | 106 | 45 |
| 3. | Corn Starch, Food Grade | 40 | 45 |
| 4. | Magnesium Stearate NF | 7 | 5 |
| | Total | 253 | 100 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the formula:

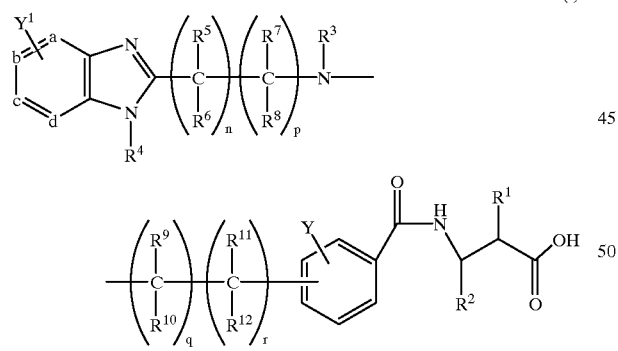

(I)

wherein n, p, q and r are each independently selected from 0 or 1;

a, b, c, and d each independently represents a carbon or nitrogen atom, with the proviso that no more than two of a, b, c, and d are nitrogen atoms;

Y and $Y^1$ each independently represents 1–4 optional substituents selected from alkyl, alkoxy, halo, —$CF_3$, and —C(O)OH;

$R^1$ is H, alkyl, aryl, aralkyl, arylcycloalkyl, heteroaryl, cycloalkyl, heterocycloalkyl, heteroaralkyl, cycloalkylalkyl, heterocycloalkylalkyl, —$NHR^A$, —NHC(O)$R^A$, —$NHSO_2R^A$, NHC(O)$NHR^A$ or —NHC(O)$OR^A$, $R^1$ being optionally substituted by 1–3 groups selected from halo, alkyl, —$CF_3$, —CN, —$OR^B$, —$SR^B$, —$CO_2R^B$, —C(O)$R^B$, —OC(O)$R^B$, —OC(O)$OR^B$ and —$SO_2R^B$, and $R^A$ and $R^B$ are independently selected from H, alkyl, aryl, aralkyl, arylcycloalkyl, heteroaryl, cycloalkyl, heterocycloalkyl, heteroaralkyl, cycloalkylalkyl and heterocycloalkylalkyl, with the proviso that when $R^1$ is alkyl, $R^1$ is not substituted with halo, the proviso that when $R^1$ is —$NHSO_2R^A$ or —NHC(O)$OR^A$, $R^A$ is not H, and the proviso that for —$SO_2R^B$ or —OC(O)$OR^B$, $R^B$ is not H;

$R^2$ is H, alkyl, aryl, aralkyl, arylcycloalkyl, heteroaryl, cycloalkyl, heterocycloalkyl, heteroaralkyl, cycloalkylalkyl, or heterocycloalkylalkyl, $R^2$ being optionally substituted by 1–3 groups selected from halo, alkyl, —$CF_3$, —CN, —$OR^C$, —$SR^C$, —$CO_2R^C$, —C(O)$R^C$, —OC(O)$R^C$, —OC(O)$OR^C$ and —$SO_2R^C$, wherein $R^C$ is selected from H, alkyl, aryl, aralkyl, arylcycloalkyl, heteroaryl, cycloalkyl, heterocycloalkyl, heteroaralkyl, cycloalkylalkyl and heterocycloalkylalkyl, with the proviso that when $R^2$ is alkyl, $R^2$ is not substituted with halo, and the proviso that for —$SO_2R^C$ or —OC(O)$OR^C$, $R^C$ is not H;

$R^3$ is heterocycloalkylalkyl, heterocycloalkyl, —C(O)$R^D$, —$SO_2R^E$, —C(O)$NR^FR^G$, —C(O)$NR^FSO_2R^E$, or —C(=S)$NR^FR^G$, wherein $R^D$, $R^E$, $R^F$ and $R^G$ are independently selected from H, alkyl, aryl, aralkyl, arylcycloalkyl, heteroaryl, cycloalkyl, heterocycloalkyl, cycloalkylalkyl and heterocycloalkylalkyl, or $R^F$ and $R^G$ taken together complete a 5–7 member ring containing 0 to 1 oxygen or sulfur atoms, and 1 to 2 nitrogen atoms, $R^3$ being optionally substituted by 1–3 groups selected from halo, alkyl, —$CF_3$, —CN, —$OR^H$, —$SR^H$, —$CO_2R^H$, —C(O)$R^H$, —OC(O)$R^H$, —OC(O)$OR^H$, —$SO_2R^H$ and —$NR^HR^H$, wherein $R^H$ is selected from H, alkyl, aryl, aralkyl, arylcycloalkyl, heteroaryl, cycloalkyl, heterocycloalkyl, heteroaralkyl, cycloalkylalkyl and heterocycloalkylalkyl, with the proviso that when $R^3$ is alkyl, $R^3$ is not substituted with halo, the proviso that when $R^3$ is —$SO_2R^E$ or —CO(O)$R^D$, $R^D$ and $R^E$ are not H, and the proviso that for —$SO_2R^H$ or —OC(O)$OR^H$, $R^H$ is not H;

$R^4$ is H, alkyl, aralkyl, arylcycloalkyl, cycloalkylalkyl, heterocycloalkylalkyl, heteroaralkyl, aryl, heteroaryl, cycloalkyl, or heterocycloalkyl, $R^4$ being optionally substituted by 1–3 groups selected from halo, alkyl, —$CF_3$, —CN, —$OR^J$, —$SR^J$, —$CO_2R^J$, —C(O)$R^J$, —OC(O)$R^J$, —OC(O)$OR^J$ and —$SO_2R^J$, wherein $R^J$ is selected from H, alkyl, aryl, aralkyl, arylcycloalkyl, heteroaryl, cycloalkyl, heterocycloalkyl, heteroaralkyl, cycloalkylalkyl and heterocycloalkylalkyl, with the proviso that when $R^4$ is alkyl, $R^4$ is not substituted with halo, and the proviso that for —$SO_2R^J$ or —OC(O)$OR^J$, $R^J$ is not H;

$R^5$, $R^6$, $R^7$, $R^8$, $R^9$, $R^{10}$, $R^{11}$ and $R^{12}$ are independently selected from H and $C_1-C_3$ alkyl;
and wherein

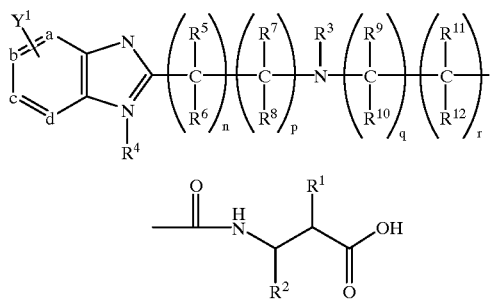

are positioned meta or para relative to each other;
or a biolabile ester thereof, or a pharmaceutically acceptable salt thereof.

2. The compound of claim 1 wherein

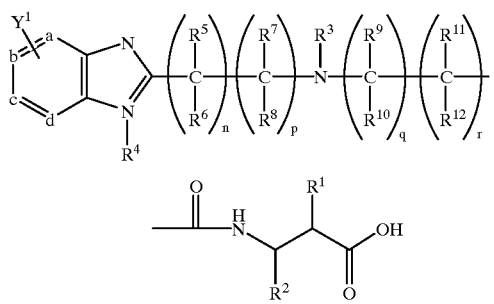

are positioned para relative to each other.

3. The compound of claim 2, wherein $R^4$ is H.

4. The compound of claim 3, wherein $R^5$, $R^6$, $R^7$, $R^8$, $R^9$, $R^{10}$, $R^{11}$ and $R^{12}$ are each H.

5. The compound of claim 4, wherein the sum of n+p is 1 and the sum of q+r is 1.

6. The compound of claim 5, wherein a, b, c, and d are each carbon atoms, and $R^2$ is H.

7. The compound of claim 6, wherein $R^3$ is selected from —C(O)$R^D$, —C(O)NR$^F$R$^G$, and —C(=S)NR$^F$R$^G$; wherein $R^D$ is selected from phenyl, alkyl, aralkyl, cycloalkyl, arylcycloalkyl, and

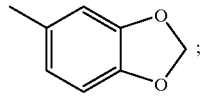

wherein $R^D$ is optionally substituted by 1–3 substituents selected from alkoxy, halo, —S—$CH_3$, phenyloxy, —OC(O)$CH_3$, —C(O)O$C_2H_5$ and —N($CH_3$)$_2$; wherein $R^F$ and $R^G$ are selected from H, alkyl, phenyl, cycloalkyl, and aralkyl; and wherein $R^F$ and $R^G$ are optionally substituted by alkoxy, halo or —$CO_2R^H$.

8. The compound of claim 7, wherein $R^1$ is H, —NHR$^A$, —NHC(O)R$^A$, —NHC(O)OR$^A$, —NHC(O)NHR$^A$ or —NHSO$_2$R$^A$.

9. The compound of claim 1, wherein said compound is selected from the group consisting of

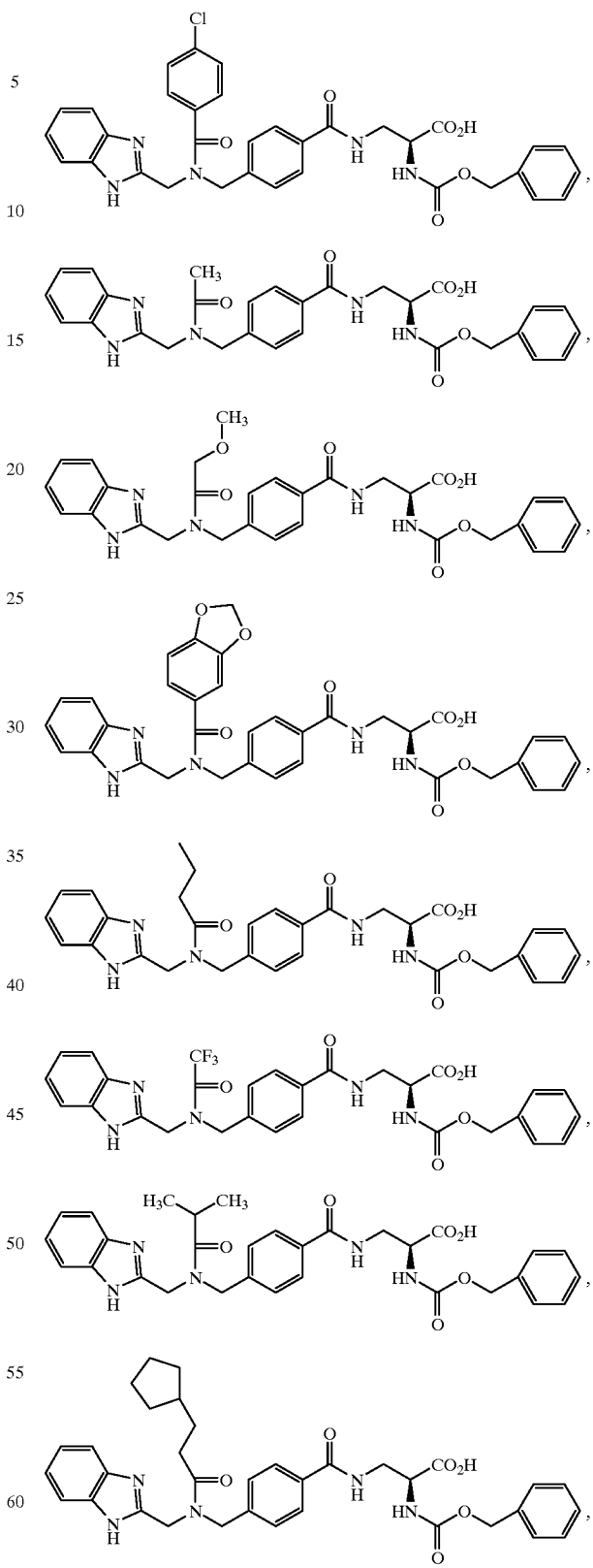

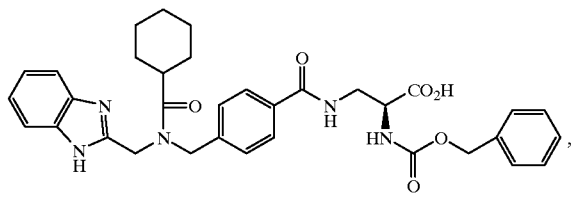
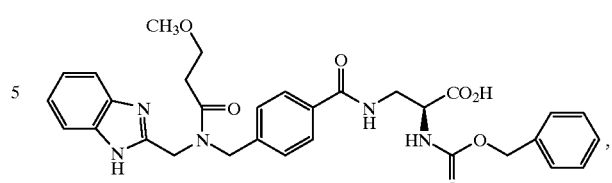
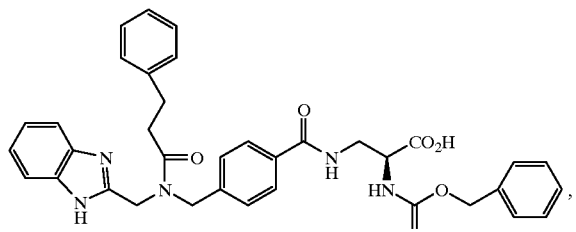
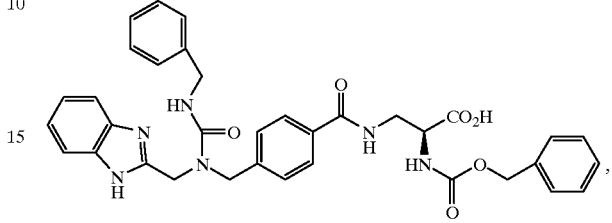
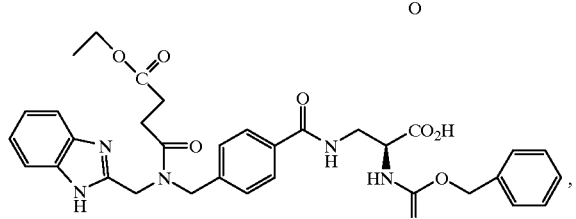
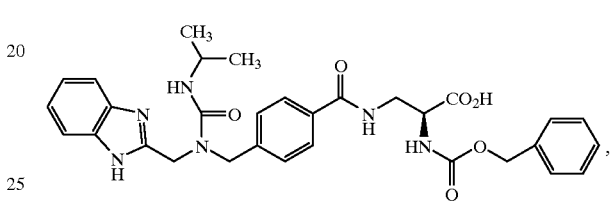
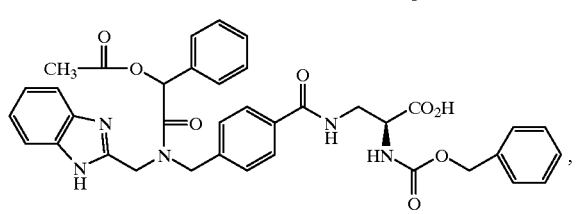
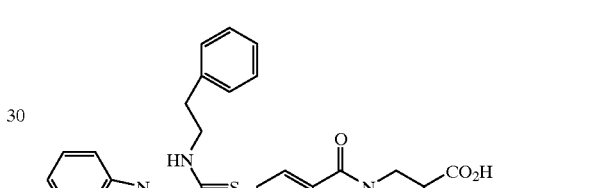
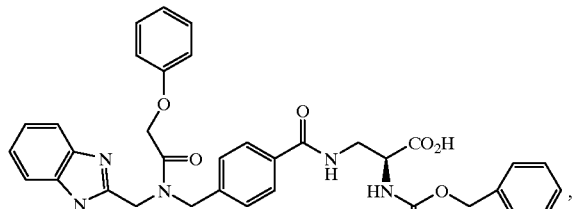
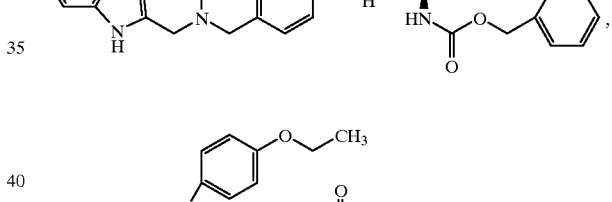
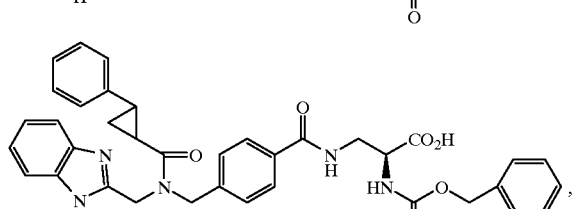
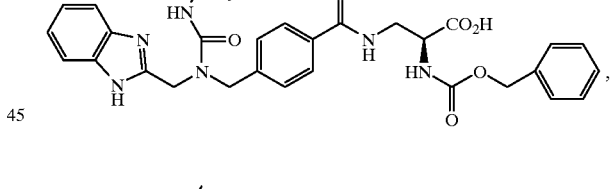
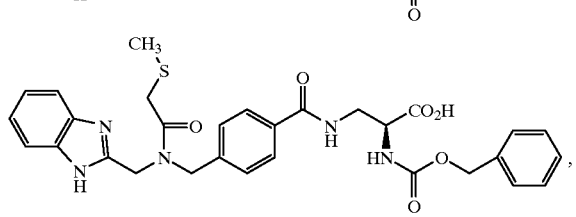
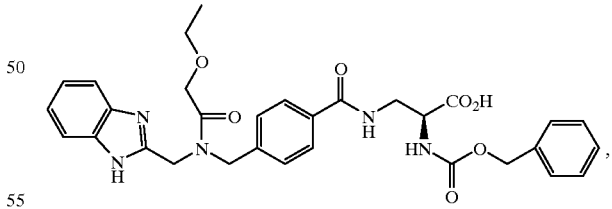
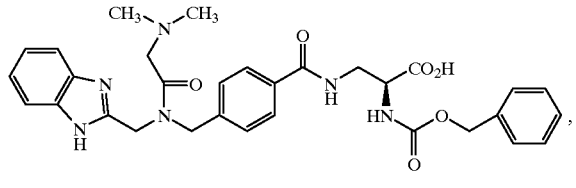
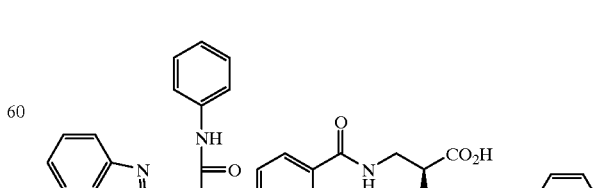
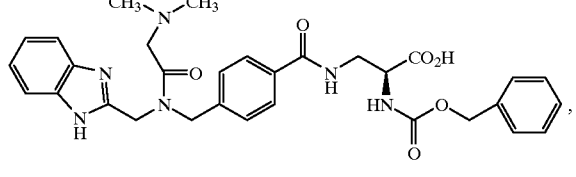
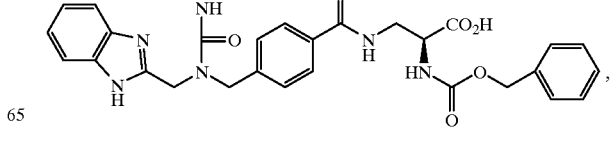

-continued

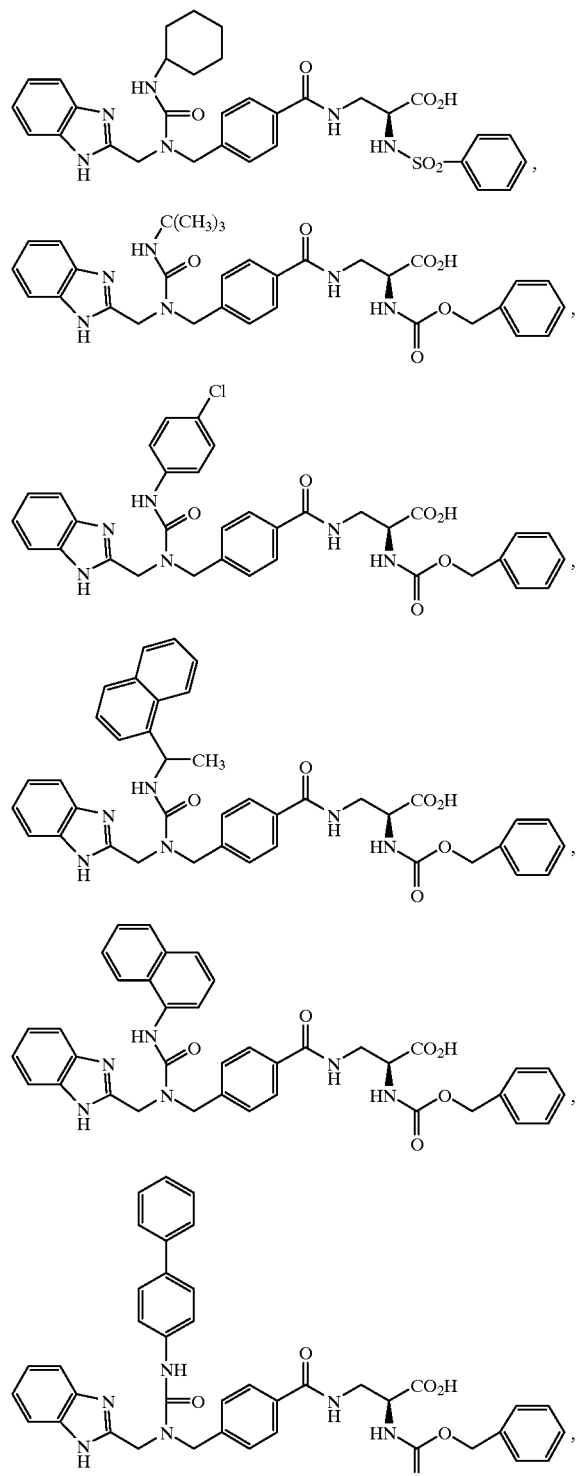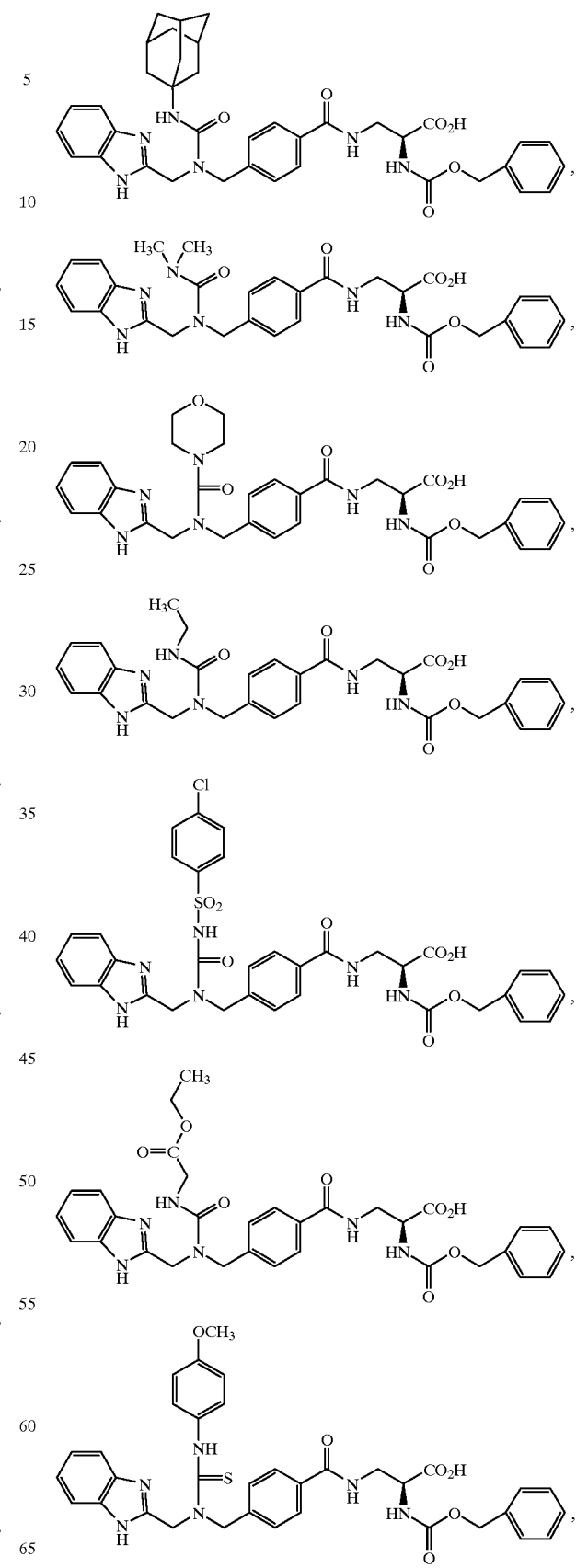

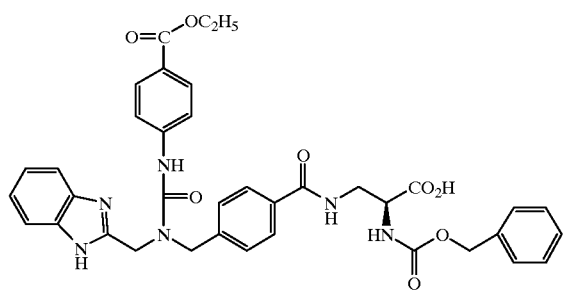
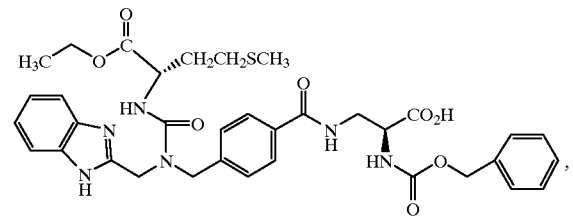
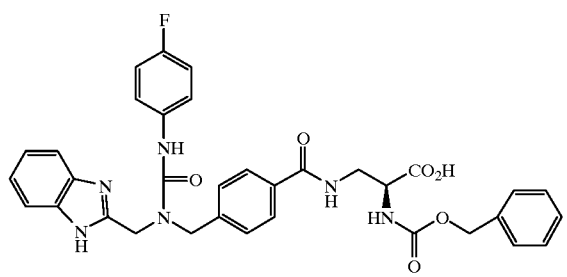
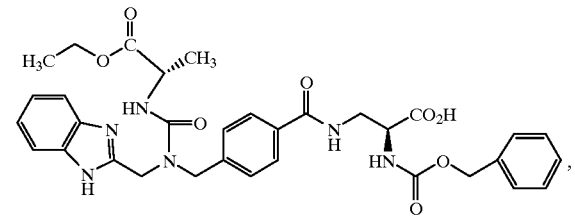
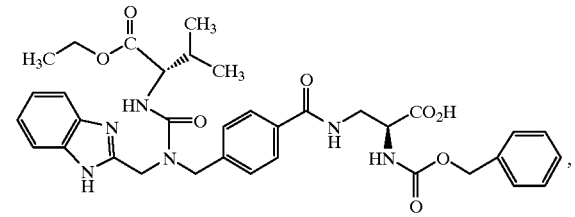
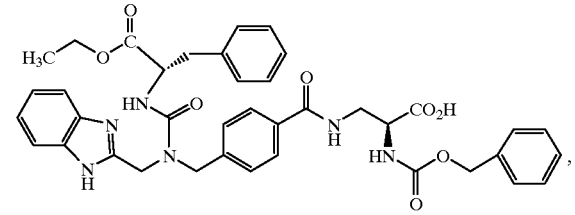
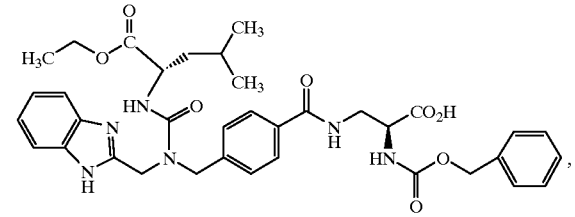
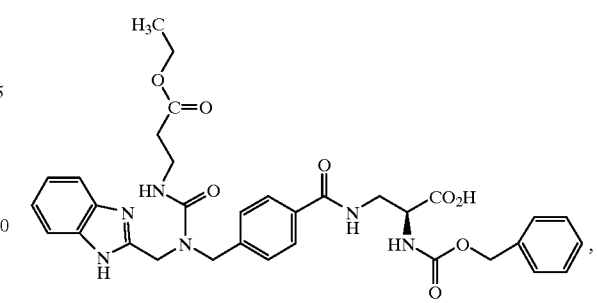
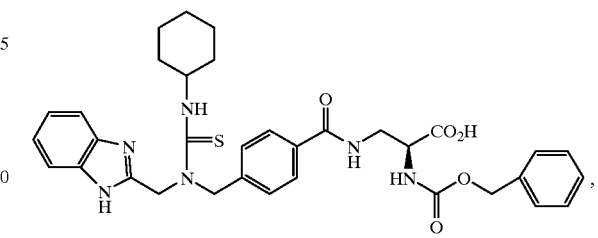
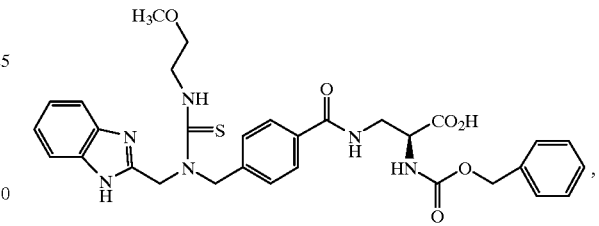
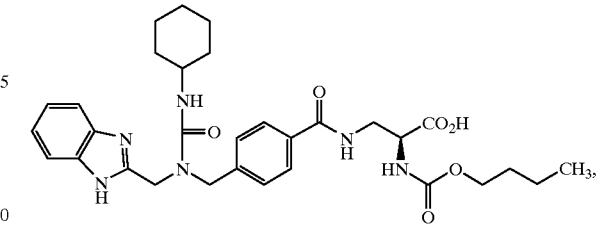
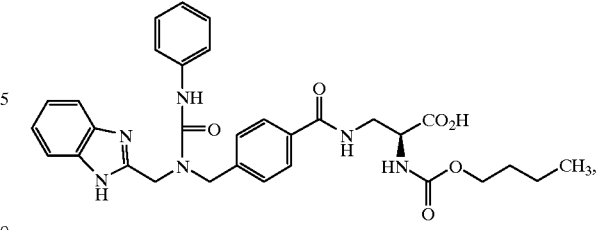
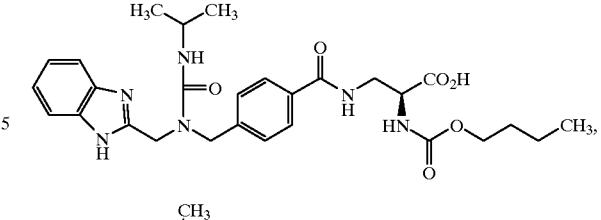
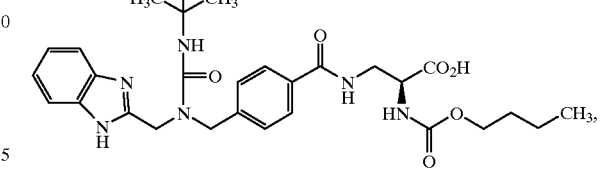

87
-continued
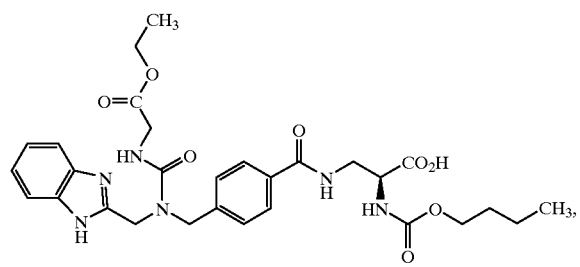
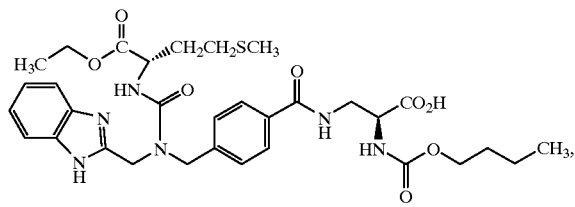
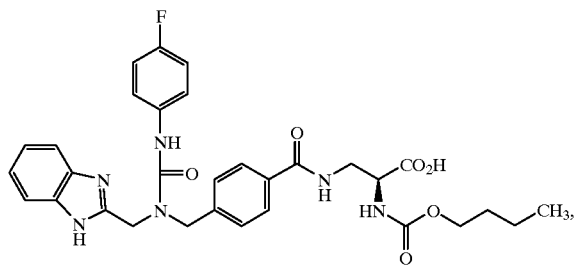
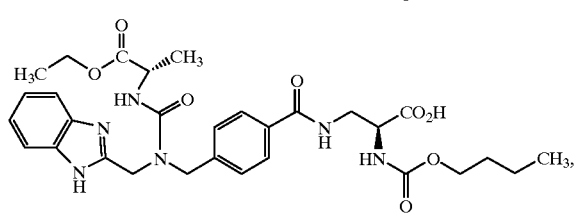
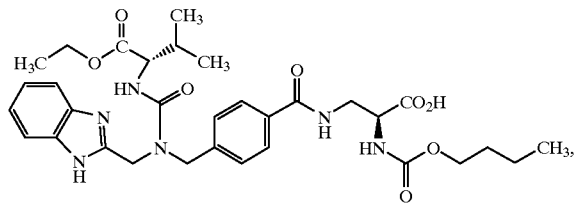
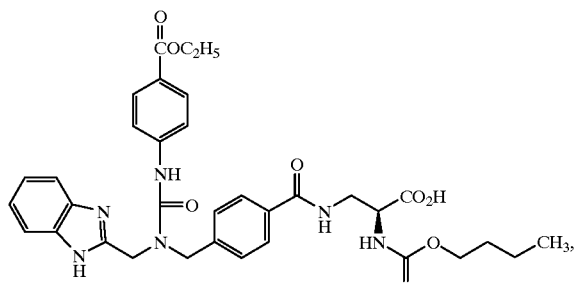
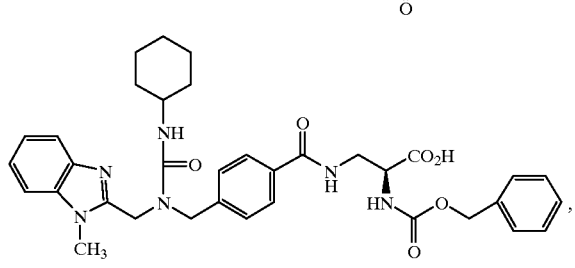
88
-continued
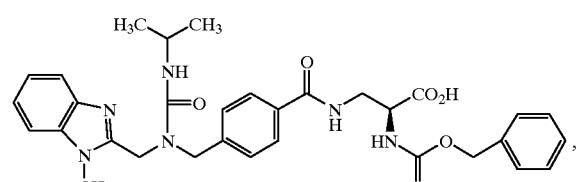
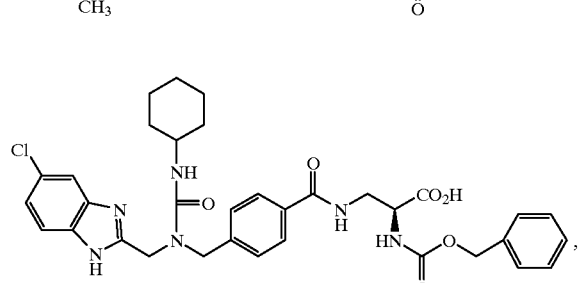
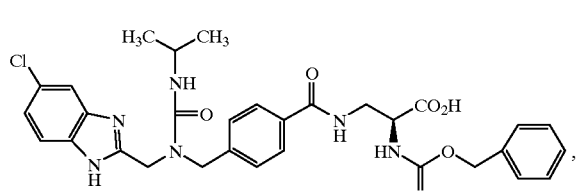
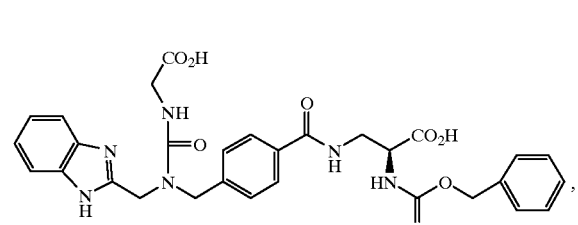
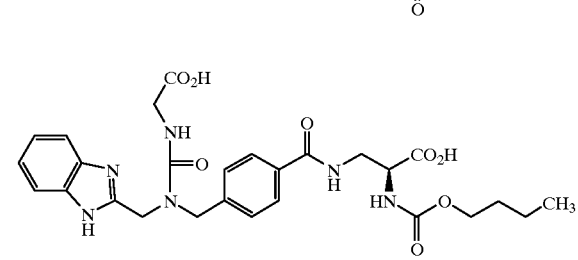
and
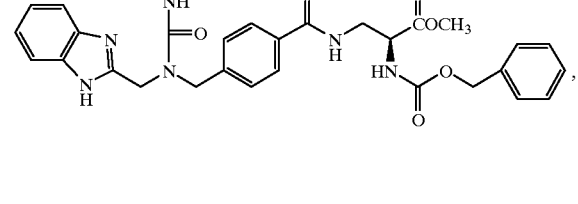
or a biolabile ester thereof, or a pharmaceutically acceptable salt thereof.

10. The compound of claim 9, wherein said compound is

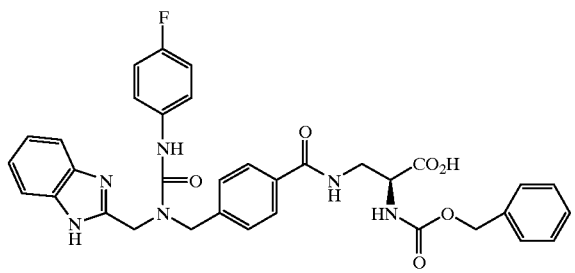

or a biolabile ester thereof, or a pharmaceutically accpetable salt thereof.

11. The ocmpound of claim 9, wherein said compound is

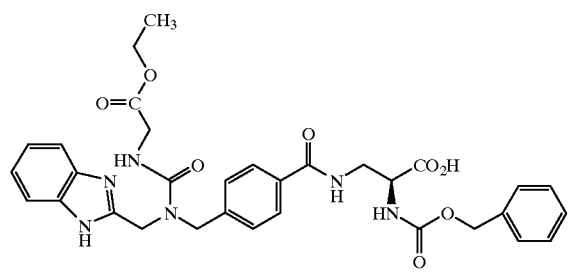

or a biolabile ester thereof, or a pharmaceutically acceptable salt thereof.

12. The compound of claim 9, wherein said compound is

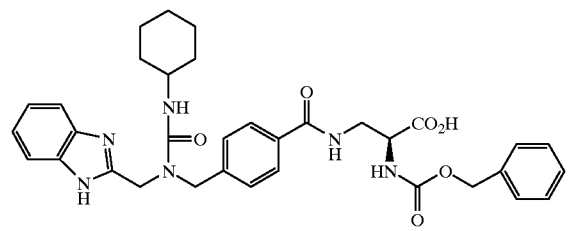

or a biolabile ester thereof, or a pharmaceutically acceptable salt thereof.

13. The compound of claim 9, wherein said compound is

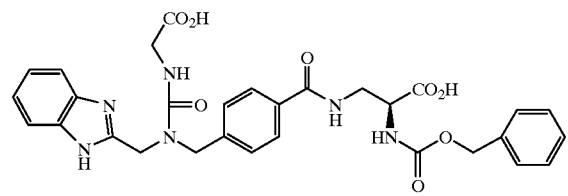

or a biolabile ester thereof, or a pharmaceutically acceptable salt thereof.

14. The compound of claim 9, wherein said compound is

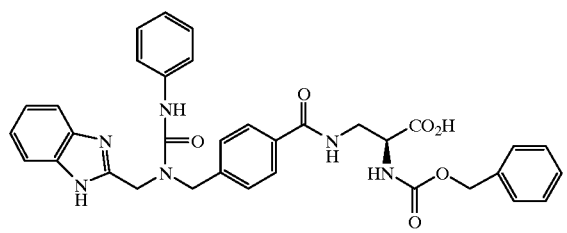

or a biolabile ester thereof, or a pharmaceutically acceptable salt thereof.

15. The compound of claim 9, wherein said compound is

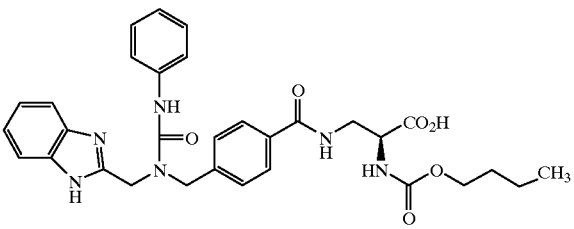

or a biolabile ester thereof, or a pharmaceutically acceptable salt thereof.

16. The compound of claim 9, wherein said compound is

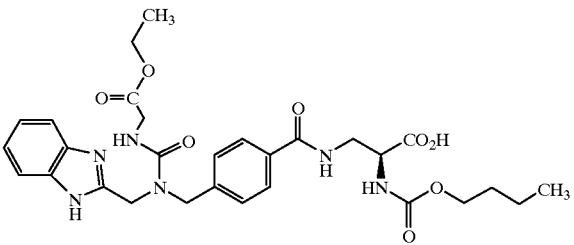

or a biolabile ester thereof, or a pharmaceutically acceptable salt thereof.

17. The compound of claim 9, wherein said compound is

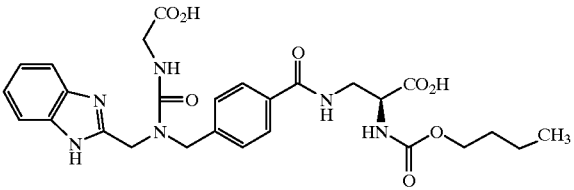

or a biolabile ester thereof, or a pharmaceutically acceptable salt thereof.

18. A method of treating a mammal afflicted with a vitronectin—mediated disorder comprising administering to said mammal an effective amount of the compound of claim 1.

19. The method of claim 18, wherein the vitronectin-mediated disorder is cancer, retinopathy, atherosclerosis, vascular restenosis, or osteoporosis.

20. The method of claim 19, wherein a, b, c, and d are each carbon atoms;

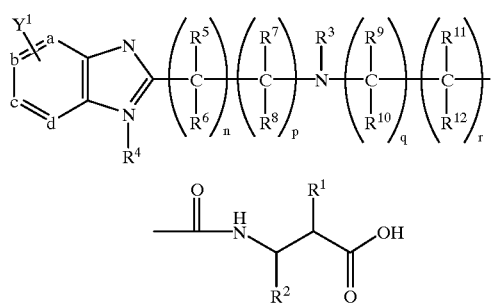

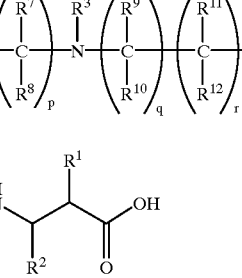

are positioned para relative to each other;

$R^2$, $R^4$, $R^5$, $R^6$, $R^7$, $R^8$, $R^9$, $R^{10}$, $R^{11}$ and $R^{12}$ are each H; the sum of n+p is 1 and the sum of q+r is 1;

$R^1$ is H, —$NHR^A$, —$NHC(O)R^A$, —$NHC(O)OR^A$, —$NHC(O)NHR^A$ or —$NHSO_2R^A$;

$R^3$ is selected from —$C(O)R^D$, —$C(O)NR^FR^G$, and —$C(=S)NR^FR^G$; wherein $R^D$ is selected from phenyl, alkyl, aralkyl, cycloalkyl, arylcycloalkyl, and

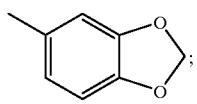

wherein $R^D$ is optionally substituted by 1–3 substituents selected from alkoxy, halo, —S—$CH_3$, phenyloxy, —OC(O)$CH_3$, —C(O)O$C_2H_5$ and —N($CH_3$)$_2$; wherein $R^F$ and $R^G$ are selected from H, alkyl, phenyl, cycloalkyl, and aralkyl; and wherein $R^F$ and $R^G$ are optionally substituted by alkoxy, halo or —$CO_2R^H$.

21. The method of claim 20, wherein the disorder is cancer.

22. The method of claim 18, wherein the disorder is cancer and the compound is selected from the group consisting of

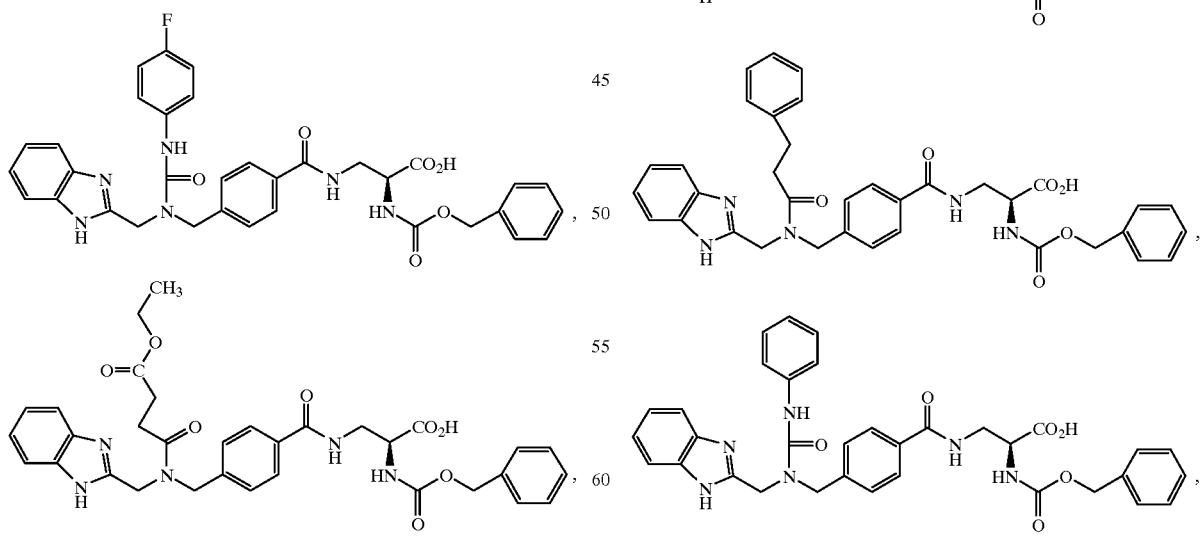

-continued

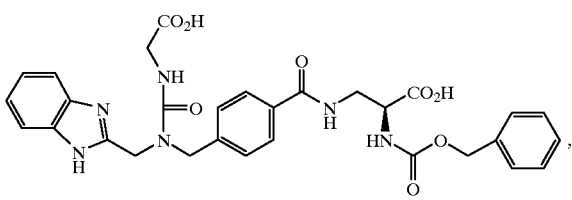

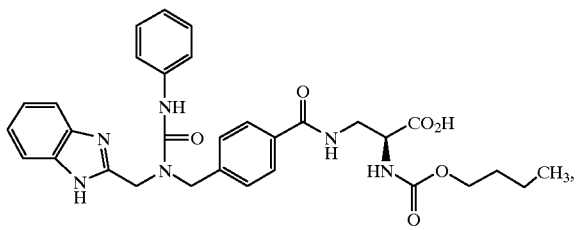

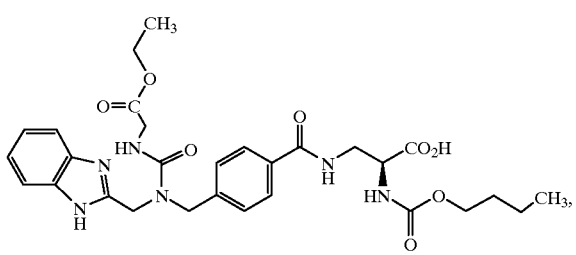

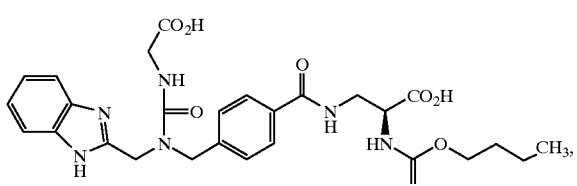

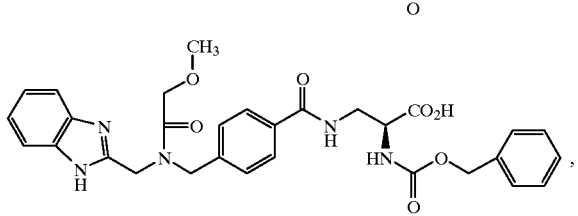

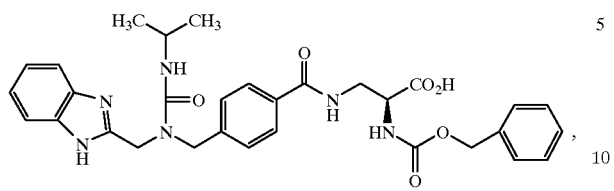
and
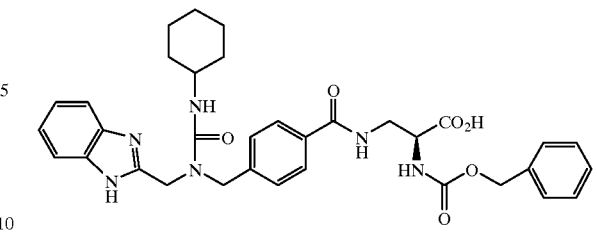
or a biolabile ester thereof, or a pharmaceutically acceptable salt thereof.
* * * * *